(12) United States Patent
Kawaura et al.

(10) Patent No.: US 8,277,481 B2
(45) Date of Patent: Oct. 2, 2012

(54) TISSUE CLOSURE AND TISSUE CLOSING DEVICE

(75) Inventors: Masakatsu Kawaura, Ashigarakami-gun (JP); Tomoji Maruyama, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 703 days.

(21) Appl. No.: 11/474,488

(22) Filed: Jun. 26, 2006

(65) Prior Publication Data

US 2006/0241579 A1    Oct. 26, 2006

Related U.S. Application Data

(63) Continuation-in-part of application No. PCT/JP2004/019734, filed on Dec. 24, 2004.

(30) Foreign Application Priority Data

Dec. 26, 2003  (JP) .................................. 2003-435843

(51) Int. Cl.
  *A61B 17/08* (2006.01)
(52) U.S. Cl. ....................................................... 606/213
(58) Field of Classification Search .................. 606/215, 606/213, 232, 151–156, 216, 217, 218
  See application file for complete search history.

(56) References Cited

U.S. PATENT DOCUMENTS

| | | | |
|---|---|---|---|
| 3,874,388 A | 4/1975 | King et al. | |
| 4,917,089 A | 4/1990 | Sideris | |
| 4,920,618 A | 5/1990 | Iguchi | |
| 5,222,974 A | 6/1993 | Kensey et al. | |
| 5,304,184 A | 4/1994 | Hathaway et al. | |
| 5,306,254 A | 4/1994 | Nash et al. | |

(Continued)

FOREIGN PATENT DOCUMENTS

EP    0 362 113 A1    4/1990

(Continued)

OTHER PUBLICATIONS

English-language translation of Official Action issued by the Patent Office of the People's Republic of China in corresponding CN Patent Application No. 200480035604.4, Apr. 4, 2008, CPO, Beijing, CN.

(Continued)

*Primary Examiner* — Corrine M McDermott
*Assistant Examiner* — Christina Lauer
(74) *Attorney, Agent, or Firm* — Buchanan Ingersoll & Rooney PC

(57) ABSTRACT

A living body tissue closing device includes an elongated body element, a clip (living body tissue closure) for closing a wound hole which penetrates a living body tissue membrane, and a thread. The body element includes a sheath, and elongated feeding and deformation arrangement. The elongated feeding and deformation arrangement includes a covered tube, a pusher tube, a thread anchoring cap, a guide wire, and a stopper. The clip includes a seal portion for covering the wound hole and a peripheral portion of the wound hole from one side of the living body tissue membrane, a deformation portion deformable between a first form in which the deformation portion can pass through the wound hole and a second form in which the deformation portion cooperates with the seal portion to sandwich the living body tissue membrane therebetween from the other side, and a fastener portion for retaining the deformation portion in the second form.

22 Claims, 21 Drawing Sheets

U.S. PATENT DOCUMENTS

| | | | |
|---|---|---|---|
| 5,350,399 A | 9/1994 | Erlebacher et al. | |
| 5,411,520 A | 5/1995 | Nash et al. | |
| 5,593,422 A | 1/1997 | Muijs Van de Moer et al. | |
| 5,662,681 A | 9/1997 | Nash et al. | |
| 5,690,674 A | 11/1997 | Diaz | |
| 5,700,277 A | 12/1997 | Nash et al. | |
| 5,702,421 A | 12/1997 | Schneidt | |
| 5,775,859 A * | 7/1998 | Anscher | 411/38 |
| 5,853,422 A | 12/1998 | Huebsch et al. | |
| 6,117,159 A * | 9/2000 | Huebsch et al. | 606/213 |
| 6,126,675 A * | 10/2000 | Shchervinsky et al. | 606/213 |
| 6,312,446 B1 | 11/2001 | Huebsch et al. | |
| 6,315,787 B1 | 11/2001 | Tsugita et al. | |
| 6,328,758 B1 * | 12/2001 | Tornier et al. | 606/232 |
| 6,508,828 B1 | 1/2003 | Akerfeldt et al. | |
| 6,596,013 B2 * | 7/2003 | Yang et al. | 606/215 |
| 6,596,014 B2 * | 7/2003 | Levinson et al. | 606/228 |
| 6,749,622 B2 | 6/2004 | McGuckin et al. | |
| 6,780,197 B2 | 8/2004 | Roe et al. | |
| 6,783,499 B2 | 8/2004 | Schwartz | |
| 2002/0173820 A1 | 11/2002 | Akerfeldt et al. | |
| 2003/0093096 A1 | 5/2003 | McGuckin et al. | |
| 2003/0144695 A1 | 7/2003 | McGuckin et al. | |
| 2004/0002681 A1 | 1/2004 | McGuckin, Jr. et al. | |
| 2004/0073242 A1 | 4/2004 | Chanduszko | |
| 2004/0133236 A1 | 7/2004 | Chanduszko | |
| 2004/0143294 A1 | 7/2004 | Corcoran et al. | |
| 2006/0135991 A1 | 6/2006 | Kawaura et al. | |

FOREIGN PATENT DOCUMENTS

| | | |
|---|---|---|
| EP | 0 534 696 A1 | 3/1996 |
| JP | 59-180109 | 10/1984 |
| JP | 59-180109 A | 10/1984 |
| JP | 1-87310 | 6/1989 |
| JP | 1-87310 U | 6/1989 |
| JP | 5-22824 | 3/1993 |
| JP | 5-22824 U | 3/1993 |
| JP | 5-212038 | 8/1993 |
| JP | 5-212038 A | 8/1993 |
| JP | 2002-360584 | 12/2002 |
| JP | 2002-360584 A | 12/2002 |
| WO | WO 00/78226 A1 | 12/2000 |
| WO | WO 2005/063133 A1 | 7/2005 |

OTHER PUBLICATIONS

Supplementary European Search Report issued Aug. 11, 2010 by the European Patent Office in European Patent Application No. 04 80 8084.

Office Action dated Nov. 16, 2010, issued by the Japanese Patent Office in corresponding Japanese Patent Application No. 2003-435843, and English language translation of Office Action.

* cited by examiner

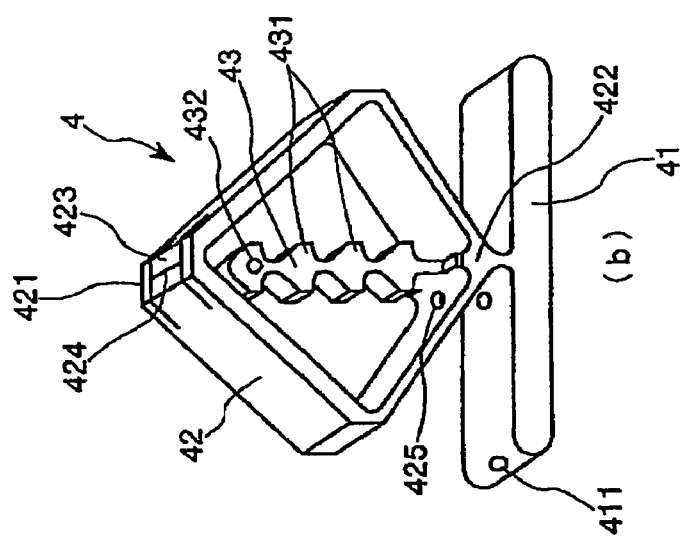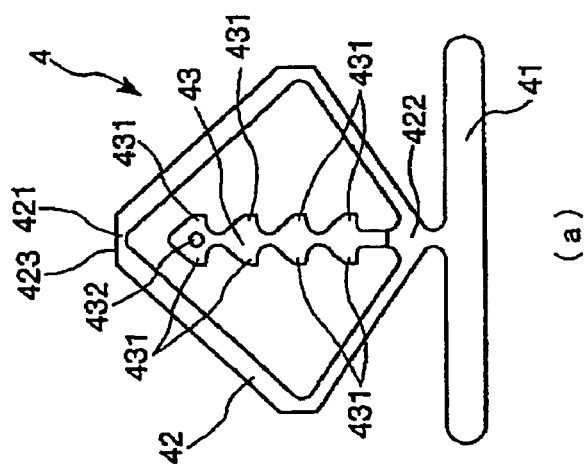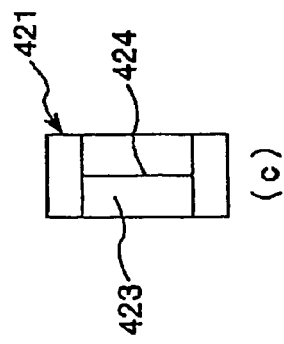
Fig. 2

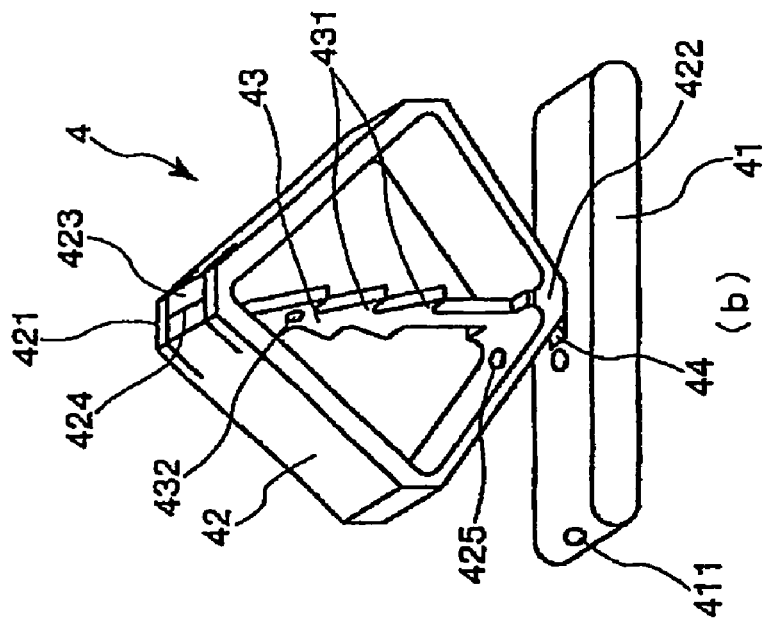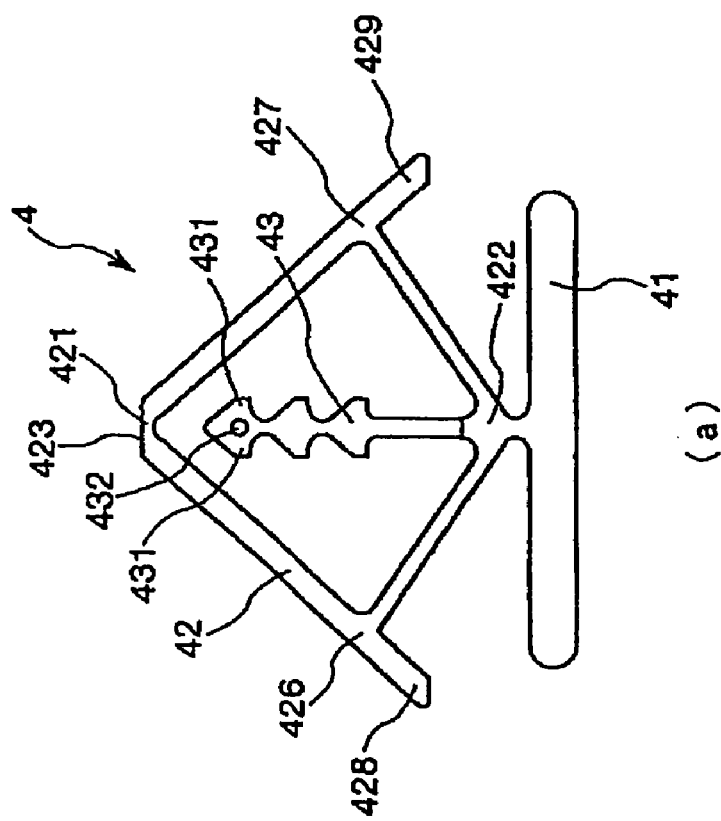
Fig. 4

TISSUE CLOSURE AND TISSUE CLOSING DEVICE

This application is a continuation-in-part of international Application No. PCT/JP2004/019734 filed on Dec. 24, 2004 and published in English.

TECHNICAL FIELD

This invention generally relates to a tissue closure and a tissue closing device for living being. More specifically, this invention pertains to a living body tissue closure and a living body tissue closing device.

BACKGROUND DISCUSSION

Low-invasion operations carried out by inserting a device for diagnosis or treatment, such as a catheter, into a blood vessel or some other tissue are known and performed on a quite often basis. For example, to treat a constriction of the coronary artery of the heart, it is necessary to insert a device such as a catheter into a blood vessel in order to perform therapeutic treatment on the constriction.

This insertion of an instrument such as a catheter into a blood vessel is normally performed through a puncture formed by dissecting or puncturing the femoral region. After the therapeutic treatment is completed, it is necessary to perform a staunching operation to stop the bleeding through the puncture. However, since the blood pressure upon bleeding (bleeding blood pressure) from the femoral artery is relatively high, it is oftentimes necessary for a person involved in the medical procedure to use a finger of their hand to press down on the site for a relatively long period of time.

In recent years, to perform the stoppage of bleeding more readily and with greater certainty, a suturing device has been developed which is adapted to be inserted through a wound hole to suture a hole formed in a blood vessel. For example, Japanese Translation of PCT for Patent No. Hei 8-504618 (corresponding to U.S. Pat. No. 5,304,184) discloses a suturing device configured such that a member which is expandable into a shape of a basket is provided at an end portion of the suturing device. Upon suturing, the member is inserted into a blood vessel and expanded into the shape of a basket, and then a suture needle is inserted. Thereafter, the member expanded in the shape of the basket is closed to catch the needle and then the end portion of the device is pulled off.

However, this suturing device can be somewhat problematic in that the reliability in catching the needle is relatively low. Further, after a thread for suturing is threaded once through the needle, it is necessary to replace the thread.

Therefore, the use of this suturing device requires additional lime and labor for suturing.

Japanese Patent No. 2,562,007 (corresponding to U.S. Pat. No. 5,306,254) discloses a living body tissue closing device in which a hard seal portion and collagen sponge are connected to each other by a thread.

The operational method associated with the use of this device involves inserting the distal end of the body element of the device into a blood vessel through a wound hole, and expanding a seal portion. Then, while the body element is pulled off slowly, the seal portion is placed into contact with the wound hole and peripheral tissue of the wound hole. If the body element is pulled off while the seal portion catches the wound hole, then the collagen sponge is expanded in the tissue on the wound hole from the distal end of the body element. Then, the body element is pulled off to the outside of the body and the thread which connects the seal portion and the collagen sponge is pulled to advance a knot and draw the seal portion and the collagen sponge toward each other to stop the bleeding. Finally, the thread is cut to complete the operation.

However, with this living body tissue closing device, the collagen sponge is propelled toward the wound hole from the body element having a diameter substantially the same as that of the wound hole. Therefore, the living body tissue closing device has a problem in that the collagen sponge is inserted into the blood vessel.

Further, with this living body tissue closing device, the collagen sponge is sometimes expanded within the distal end of the body element and does not come out of the body element.

Further, since the seal portion and the collagen sponge are connected to each other by the thread, one of the seal portion and the collagen sponge is capable of being displaced in any direction with respect to the other. Therefore, the angle changes to an unexpected direction, and operation of the living body tissue closing device is difficult.

Japanese Patent No. 3,133,059 (corresponding to U.S. Pat. No. 5,593,422) discloses a device in which a closing member with a thread attached thereto is disposed in a blood vessel, a ring (locking member) is moved along the thread, and the ring locks the thread outside the blood vessel to close up the opening formed in the wall of the blood vessel.

According to the device described, the closing member is secured to the wall of the blood vessel by fixing the ring to the thread.

However, in this just mentioned device, since the fixing operation involving securing the ring to the thread must be performed within subcutaneous tissues, the fixing operation can be difficult to perform.

Also, since the outside diameter of the ring needs to be dimensioned so that the ring can be inserted into the opening, the ring must necessarily be relatively small in size, and there is the possibility that the ring may drop into the blood vessel through the opening formed in the wall of the blood vessel.

Further, since the closing member and the ring are connected to each other by the thread, one of the closing member and the ring is capable of being displaced in any direction with respect to the other. Therefore, the angle between the two can change in an unexpected direction, and the living body tissue closing device is thus difficult to operate.

SUMMARY

According to one aspect, a tissue closure for closing an opening which penetrates a tissue membrane includes a seal portion having a flat face portion for covering the opening and a surrounding portion of the opening from one side of the tissue membrane, a deformation portion capable of expanding and contracting in two directions substantially perpendicular to each other, and a fastener portion positioned on the inner side of the deformation portion for retaining the deformation portion in a predetermined form, the deformation portion having an opening portion movable relative to the fastener portion and capable of accepting the fastener portion and a fixed portion integrated with the fastener portion and immovably with respect to the fastener portion.

With the tissue closure, a stanching operation for an opening formed in a tissue membrane such as a blood vessel wall can be performed readily with a higher degree of accuracy and with a high degree of safety. In other words, the opening can be closed readily and with certainty, and the bleeding can be stanched completely.

In the tissue closure of the present invention, preferably the seal portion and the deformation portion are formed integrally from the same material.

In the tissue closure of the present invention, preferably the deformation portion has a shape of a framework.

In the tissue closure of the present invention, preferably the deformation portion has a quadrangular shape formed integrally from four links and deforms such that two corner portions at diagonal positions of the quadrangular shape move toward and away from each other.

In the tissue closure of the present invention, preferably the fastener portion is formed in such a manner as to control the distance between the two corner portions.

In the tissue closure of the present invention, preferably the fastener portion is formed in such a manner as to be capable of controlling the distance between the two corner portions at a plurality of stages.

In the tissue closure of the present invention, preferably the fastener portion is formed in such a manner as to be capable of controlling the degree of deformation of the deformation portion at a plurality of stages.

In the tissue closure of the present invention, preferably the fastener portion is formed in such a manner as to allow deformation of the deformation portion in a direction in which the degree of deformation of the deformation portion increases but block deformation of the deformation portion in another direction in which the degree of deformation of the deformation portion decreases.

In the tissue closure of the present invention, preferably the fastener portion has at least one pawl capable of being inserted into the opening portion and engaged with the deformation portion.

In the tissue closure of the present invention, preferably the seal portion has a shape of a plate.

In the tissue closure of the present invention, preferably the deformation portion is connected for rocking motion to the seal portion.

In the tissue closure of the present invention, preferably the fastener portion is formed integrally with the seal portion and the deformation portion from the same material.

In the tissue closure of the present invention, preferably the fastener portion and the deformation portion are individually inclined with respect to the seal portion.

In the tissue closure of the present invention, preferably the tissue closure is made of a bioabsorbable material.

In the tissue closure of the present invention, preferably the tissue closure has formed therein a hole through which a guide wire is to pass through.

In the tissue closure of the present invention, preferably the fastener portion has formed therein a hole through which a string for pulling the tissue closure is to be threaded.

In the tissue closure of the present invention, preferably the tissue membrane is a blood vessel wall, and the one side is an inner surface of the blood vessel wall.

According to another aspect of the present invention, there is provided a tissue closure for closing an opening which penetrates a tissue membrane, including, a seal portion having a shape of a plate for covering the opening and a surrounding portion of the opening from one side of the tissue membrane, a deformation portion having a shape of a framework deformable between a contracted form in which the deformation portion extends in a direction substantially perpendicular to the seal portion and is contracted in a direction substantially parallel to the seal portion and an expanded form in which the deformation portion is contracted in the direction substantially perpendicular to the seal portion and is expanded in the direction substantially parallel to the seal portion, and a fastener portion for retaining the deformation portion when the deformation portion is deformed to a predetermined form between the contracted form and the expanded form.

With the tissue closure, a stanching operation for an opening formed in a tissue membrane can be performed readily with a higher degree of accuracy and with a high degree of safety. In other words, the opening can be closed readily and with certainty, and the bleeding can be stanched completely.

In the tissue closure of the present invention, preferably the deformation portion has a shape like a pantograph.

In the tissue closure of the present invention, preferably the deformation portion has a polygonal annular shape formed by bending a belt-like member by a plural number of times.

In the tissue closure of the present invention, preferably the deformation portion has a quadrangular shape formed integrally from four links and deforms such that two corner portions at diagonal positions of the quadrangular shape move toward and away from each other.

Preferably, the tissue closure of the present invention further includes a connecting portion for connecting the seal portion and the deformation portion to each other.

In the tissue closure of the present invention, preferably the deformation portion has a projection provided on the outer side thereof on the seal portion side and projecting toward the seal portion side.

With the tissue closure, the projection is positioned in the proximity of the opening closed with the tissue closure, and the opening is tightened strongly by the projection. Consequently, the bleeding can be stanched with a higher degree of certainty.

Further, even if failure in stanching (for example, when the blood vessel wall or the subcutaneous tissue is so hard that the deformation portion cannot be expanded or the like) occurs and manual compression becomes required and force in the direction in which the tissue closure is inserted transcutaneously into the blood vessel is applied to the tissue closure by the manual compression, a drop (omission) of the tissue closure into the blood vessel can be prevented by the projection. This enhances the safety.

According to a further aspect of the present invention, there is provided a tissue closure having a seal portion for covering an opening which penetrates a tissue membrane and a surrounding portion of the opening from one side of the tissue membrane, the tissue closure being adapted to close the opening, the tissue closure comprising: at least at a portion having a framework body deformable between a contracted form in which the portion is extended in a direction substantially perpendicular to a reference plane and is contracted in a direction substantially parallel to the reference plane and an expanded form in which the portion is contracted in the direction substantially perpendicular to the reference plane and is expanded in the direction substantially parallel to the reference plane.

With the tissue closure, a stanching operation for an opening formed in a tissue membrane such as a blood vessel wall can be performed readily with a higher degree of accuracy and with a high degree of safety. In other words, the opening can be closed readily and with certainty, and the bleeding can be stanched completely.

In the tissue closure of the present invention, preferably the tissue closure has a fastener portion for retaining the portion when the framework body is placed into a predetermined form between the contracted form and the expanded form. According to a still further aspect of the present invention, there is provided a tissue closure for closing an opening which penetrates a tissue membrane of a living organism lumen, including, a seal portion for being inserted into the living organism lumen to cover the opening and a surrounding portion of the opening from an inner surface of the tissue membrane, the seal portion being formed such that the longest portion thereof has a length set smaller than the inner diameter of the living organism lumen into which the seal portion is inserted.

With the tissue closure, a stanching operation for an opening formed in a tissue membrane such as a blood vessel wall can be performed readily with a higher degree of accuracy and with a high degree of safety. In other words, the opening can be closed (closed up) readily and with certainty, and the bleeding can be stanched completely.

Preferably, the tissue closure of the present invention further includes a deformation portion deformable between a first form in which the deformation portion can pass through the opening and a second form in which the deformation portion can cooperate with the seal portion to sandwich the tissue membrane therebetween from the other side of the tissue membrane.

Preferably, the tissue closure of the present invention further includes a fastener portion for retaining the deformation portion in the second form.

In the tissue closure of the present invention, preferably the seal portion is connected for turning motion around an axis of turning motion to the deformation portion.

In the tissue closure of the present invention, preferably the seal portion has a shape of a plate, and the length of the longest portion of the seal portion is 6 mm or less.

According to a yet further aspect of the present invention, there is provided a tissue closure for closing an opening which penetrates a tissue membrane, including, a seal portion for covering the opening and a surrounding portion of the opening from one side of the tissue membrane, and a retaining portion for cooperating with the seal portion to sandwich the tissue membrane therebetween from the other side of the tissue membrane and retain the seal portion on the one side, the retaining portion having the seal portion connected thereto for turning motion around an axis of turning motion.

With the tissue closure, a stanching operation for an opening formed in a tissue membrane such as a blood vessel wall can be performed readily with a higher degree of accuracy and with a high degree of safety. In other words, the opening can be closed readily and with certainty, and the bleeding can be stanched completely.

In the tissue closure of the present invention, preferably a connecting portion between the seal portion and the retaining portion has flexibility such that, as the connecting portion is bent, the seal portion is turned.

In the tissue closure of the present invention, preferably the seal portion has a shape of a plate, and the retaining portion has a shape of a framework deformable between a first form in which the retaining portion can pass through the opening and a second form in which the retaining portion can cooperate with the seal portion to sandwich the tissue membrane therebetween from the other side of the tissue membrane.

According to a yet further aspect of the present invention, there is provided a tissue closing device, including, any tissue closure of the present invention, and an elongated arrangement device for removably retaining, at a distal end portion thereof, the tissue closure, the tissue closure being adapted to be arranged into a living organism and close an opening which penetrates a tissue membrane.

With the tissue closing device, a stanching operation for an opening formed in a tissue membrane such as a blood vessel wall can be performed readily with a higher degree of accuracy and with a high degree of safety.

In other words, the opening can be closed (closed up) readily and with certainty, and the bleeding can be stanched completely.

Preferably, the tissue closing device of the present invention further includes displacement means for displacing the seal portion so that the seal portion may extend substantially in parallel to an axial direction of the arrangement device.

In the tissue closing device of the present invention, preferably the displacement means has a contacting portion provided at the distal end portion of the arrangement device for contacting with a face of the seal portion on the deformation portion side.

In the tissue closing device of the present invention, preferably the tissue closure includes a deformable deformation portion adjacent the seal portion, and the tissue closing device further includes a retainer for retaining the deformation portion of the tissue closure at the distal end portion of the arrangement device.

In the tissue closing device of the present invention, preferably the retainer includes a deformation portion pulling means for pulling the deformation portion to a proximal end side of the arrangement device.

According to a yet further aspect of the present invention, there is provided a tissue closing device for closing an opening which penetrates a tissue membrane, including, . . . an elongated body element having a distal end portion capable of passing though the opening, a tissue closure removably mounted at the distal end portion of the body element and capable of passing through the opening together with the distal end portion of the body element to close the opening, and a deformation means, the tissue closure including, a seal portion for covering the opening and a surrounding portion of the opening from one side of the tissue membrane, a deformation portion having a shape of a framework deformable to a first form in which the deformation portion can pass through the opening and deformable by the deformation means to a second form in which the deformation portion cooperates with the seal portion to sandwich the tissue membrane therebetween from the opposite side of the tissue membrane, and a fastener portion for retaining the deformation portion in the second form.

With the tissue closing device, a stanching operation for an opening formed in a tissue membrane such as a blood vessel wall can be performed readily with a higher degree of accuracy and with a high degree of safety.

In other words, the opening can be closed (closed up) readily and with certainty, and the bleeding can be stanched completely.

According to a yet further aspect of the present invention, there is provided a tissue closing device for closing an opening which penetrates a tissue membrane, including, an elongated body element having a distal end portion capable of passing though the opening, a tissue closure removably mounted at the distal end portion of the body element and capable of passing through the opening together with the distal end portion of the body element to close the opening, and deformation means, the tissue closure including, a seal portion for covering the opening and a surrounding portion of the opening from one side of the tissue membrane, a deformation portion deformable to a first form in which the deformation portion can pass through the opening and deformable by the deformation means to a second form in which the deformation portion cooperates with the seal portion to sandwich the tissue membrane therebetween from the opposite side of the tissue membrane, and a fastener portion for retaining the deformation portion in the second form, the seal portion and the deformation portion being formed integrally from the same material.

With the tissue closing device, a stanching operation for an opening formed in a tissue membrane such as a blood vessel wall can be performed readily with a higher degree of accuracy and with a high degree of safety.

In other words, the opening can be closed readily and with certainty, and the bleeding can be stanched completely.

In the tissue closing device of the present invention, preferably the deformation portion has a shape of a framework.

In the tissue closing device of the present invention, preferably the deformation portion has an opening portion into which at least part of the fastener portion can be inserted.

In the tissue closing device of the present invention, preferably the fastener portion has at least one pawl capable of being inserted into the opening portion and engaged with the deformation portion.

In the tissue closing device of the present invention, preferably the deformation portion has a quadrangular shape formed integrally from four links and deforms such that two corner portions at diagonal positions of the quadrangular shape move toward and away from each other.

In the tissue closing device of the present invention, preferably the fastener portion is formed in such a manner as to control the distance between the two corner portions.

In the tissue closing device of the present invention, preferably the fastener portion is formed in such a manner as to be capable of controlling the distance between the two corner portions at a plurality of stages.

In the tissue closing device of the present invention, preferably the fastener portion is formed in such a manner as to be capable of controlling the degree of deformation of the deformation portion at a plurality of stages.

In the tissue closing device of the present invention, preferably the fastener portion is formed in such a manner as to allow deformation of the deformation portion in a direction in which the degree of deformation of the deformation portion increases but block deformation of the deformation portion in another direction in which the degree of deformation of the deformation portion decreases when the deformation portion is in the second form.

In the tissue closing device of the present invention, preferably the seal portion has a shape of a plate.

In the tissue closing device of the present invention, preferably the deformation portion is connected for rocking motion to the seal portion.

In the tissue closing device of the present invention, preferably the fastener portion is formed integrally with the seal portion and the deformation portion from the same material.

In the tissue closing device of the present invention, preferably the fastener portion and the deformation portion are individually inclined with respect to the seal portion.

In the tissue closing device of the present invention, preferably the tissue closure is made of a bioabsorbable material.

In the tissue closing device of the present invention, preferably the tissue closure has formed therein a hole through which a guide wire is to pass through.

Preferably, the tissue closing device of the present invention further includes pulling means for pulling the tissue closure, the deformation portion being deformed by the deformation means while the tissue closure is being pulled by the pulling means.

In the tissue closing device of the present invention, preferably the pulling means is a string.

In the tissue closing device of the present invention, preferably the fastener portion has a hole through which the string is to be threaded.

In the tissue closing device of the present invention, preferably the deformation means presses the deformation portion to deform the deformation portion into the second form.

In the tissue closing device of the present invention, preferably the deformation means is, at least at a portion thereof, a tubular member provided on the body element.

In the tissue closing device of the present invention, preferably the tissue membrane is a blood vessel wall, and the one side is an inner surface of the blood vessel wall while the opposite side is an outer surface of the blood vessel wall.

BRIEF DESCRIPTION OF THE DRAWING FIGURES

FIG. 1 is a perspective view of a first embodiment of a tissue closing device as disclosed herein.

FIGS. 2(a)-(c) are an elevational view, a perspective view and a partial plan view respectively of the tissue closure forming a part of the tissue closing device shown in FIG. 1.

FIG. 3 is a side elevational view showing different examples of a configuration of the tissue closure of the tissue closing device shown in FIG. 1.

FIGS. 4(a) and 4(b) are a side elevational view and a perspective view respectively of further examples of a configuration of the tissue closure of the tissue closing device shown in FIG. 1.

Figure 13:
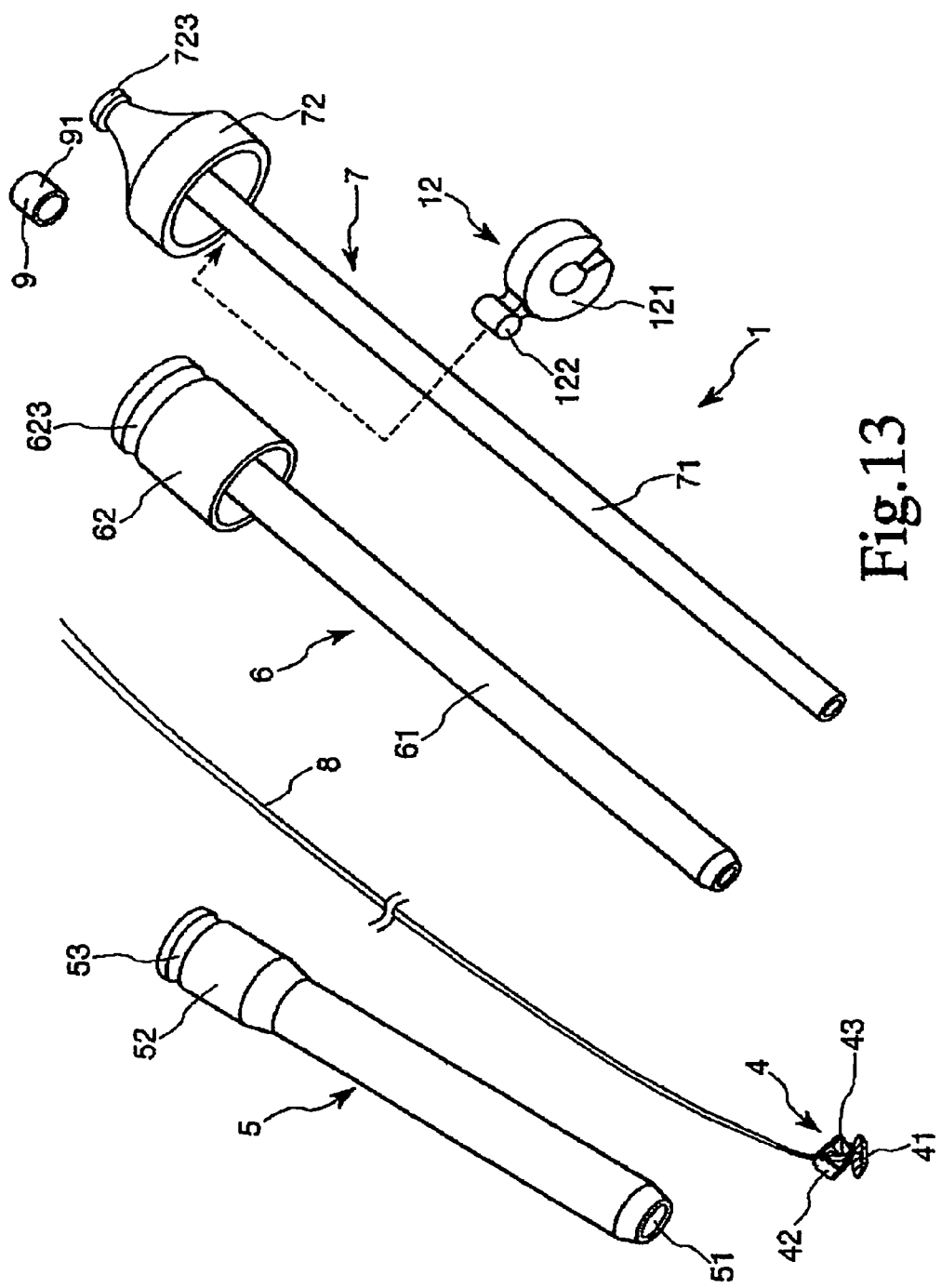
FIG. 13 is a perspective view of a second embodiment of a tissue closing device disclosed herein.

FIGS. 14(a)-(d) are perspective views of different operational aspects of the tissue closure of the tissue closing device shown in FIG. 13.

Figure 15:
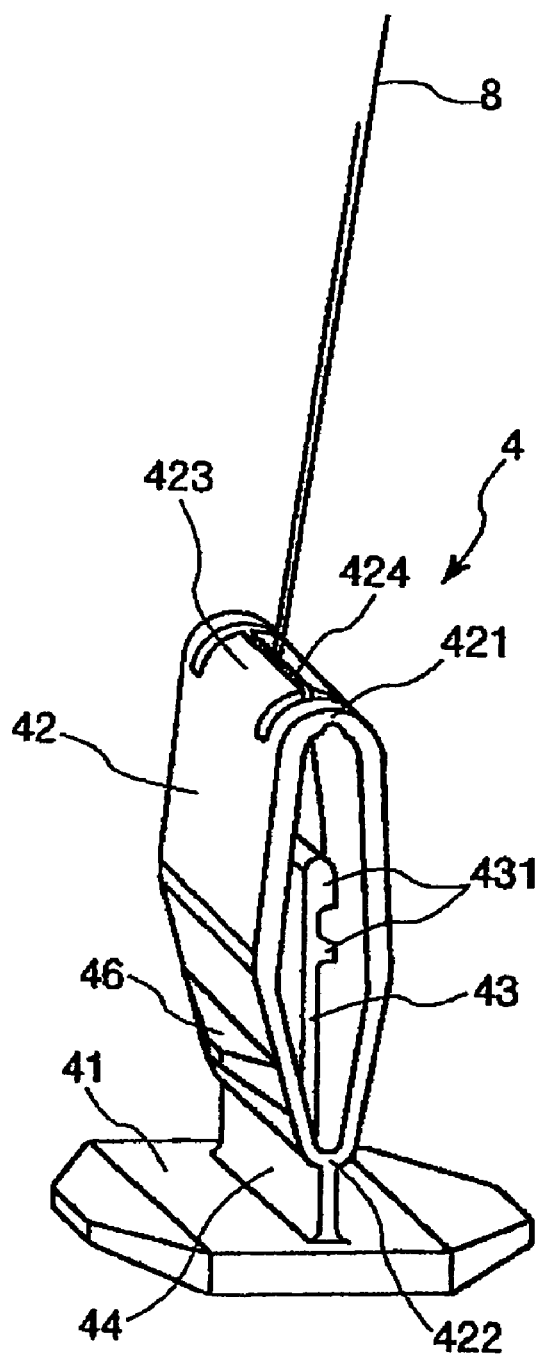

FIG. 15 is a perspective view of another example of a configuration of the tissue closure of the tissue closing device shown in FIG. 13.

Figure 16:
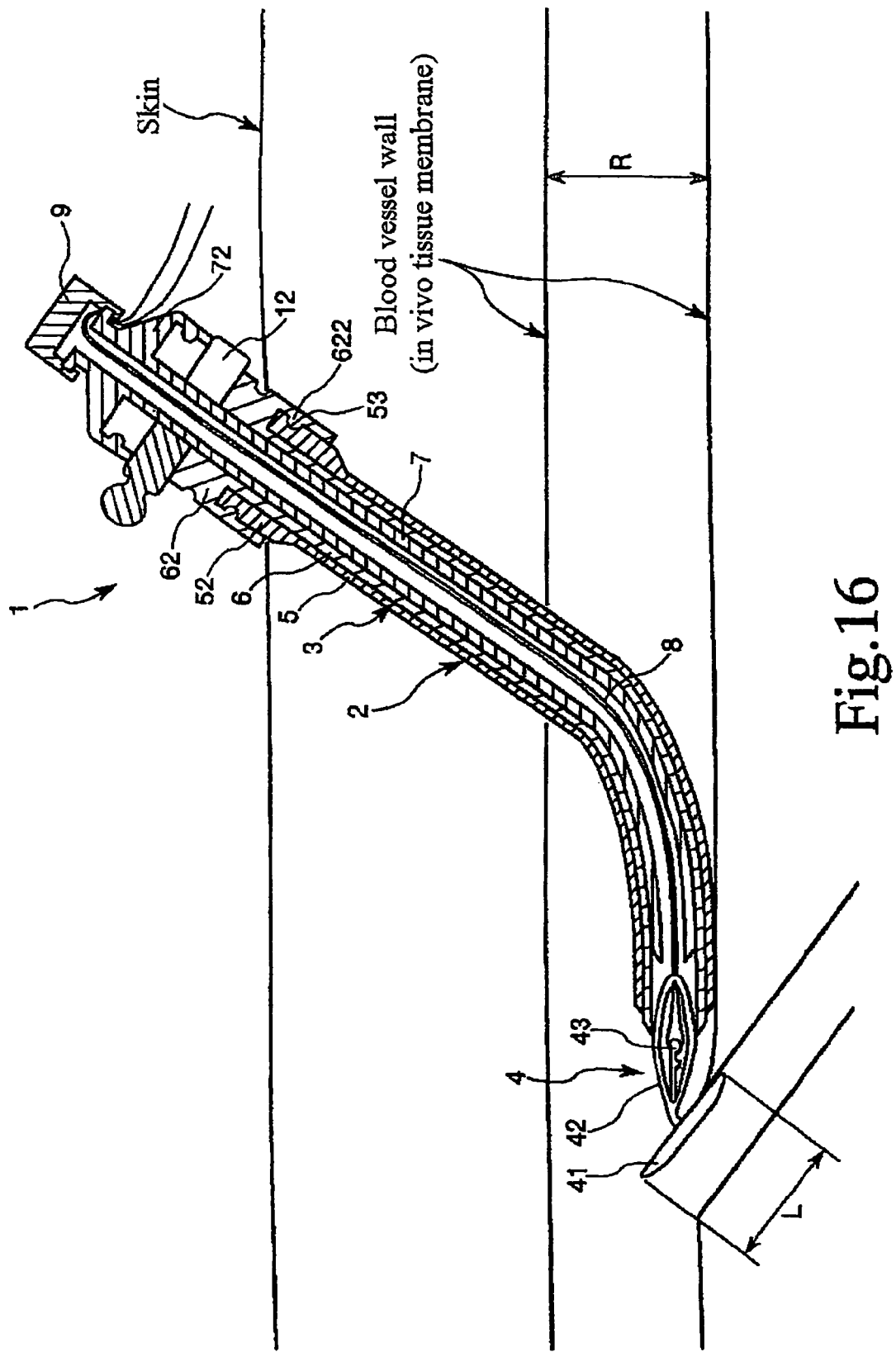

FIG. 16 is a sectional view illustrating an operational aspect of the tissue closing device shown in FIG. 13.

Figure 17:
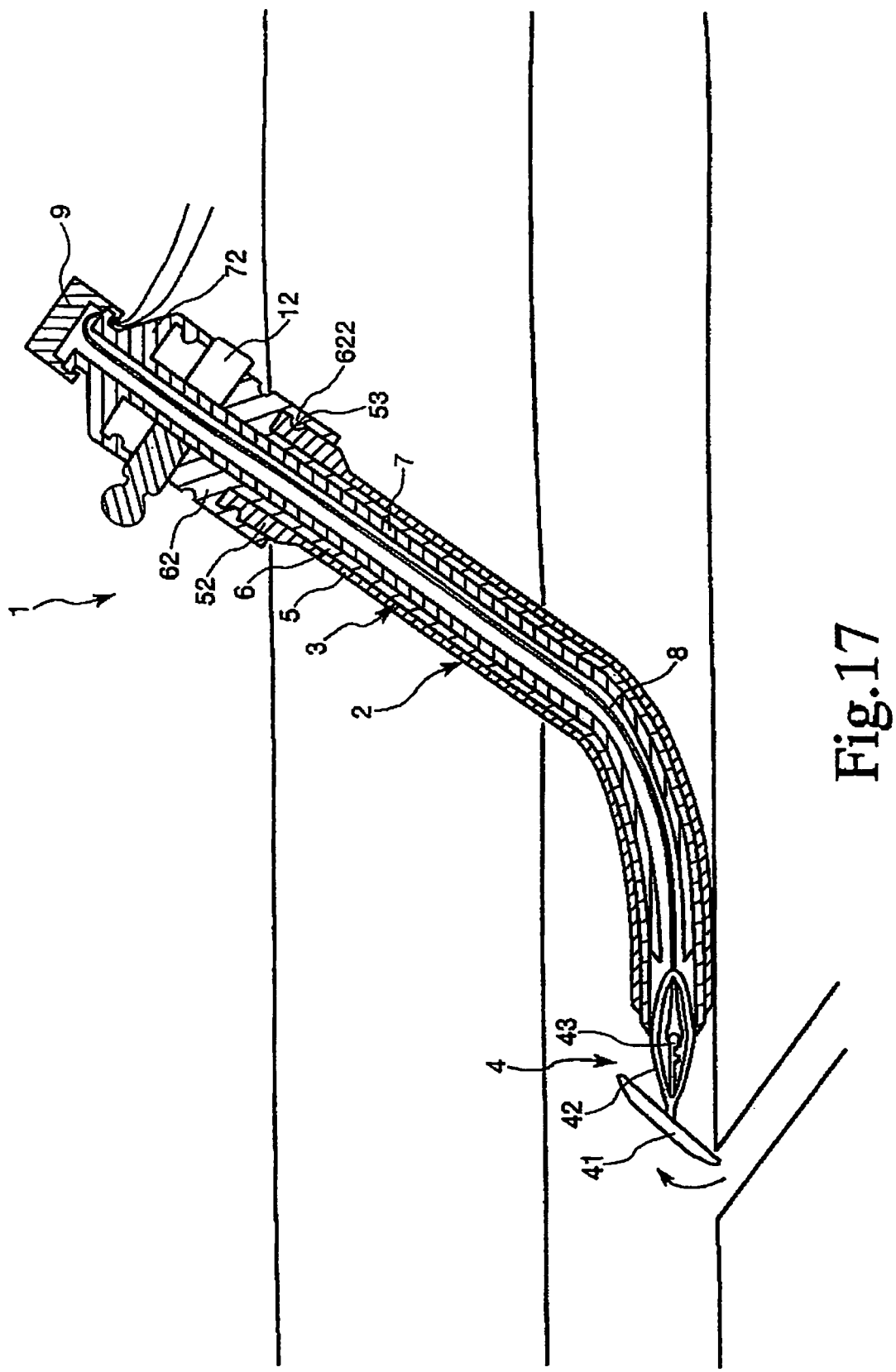

FIG. 17 is a sectional view illustrating another operational aspect of the tissue closing device shown in FIG. 13.

Figure 18:
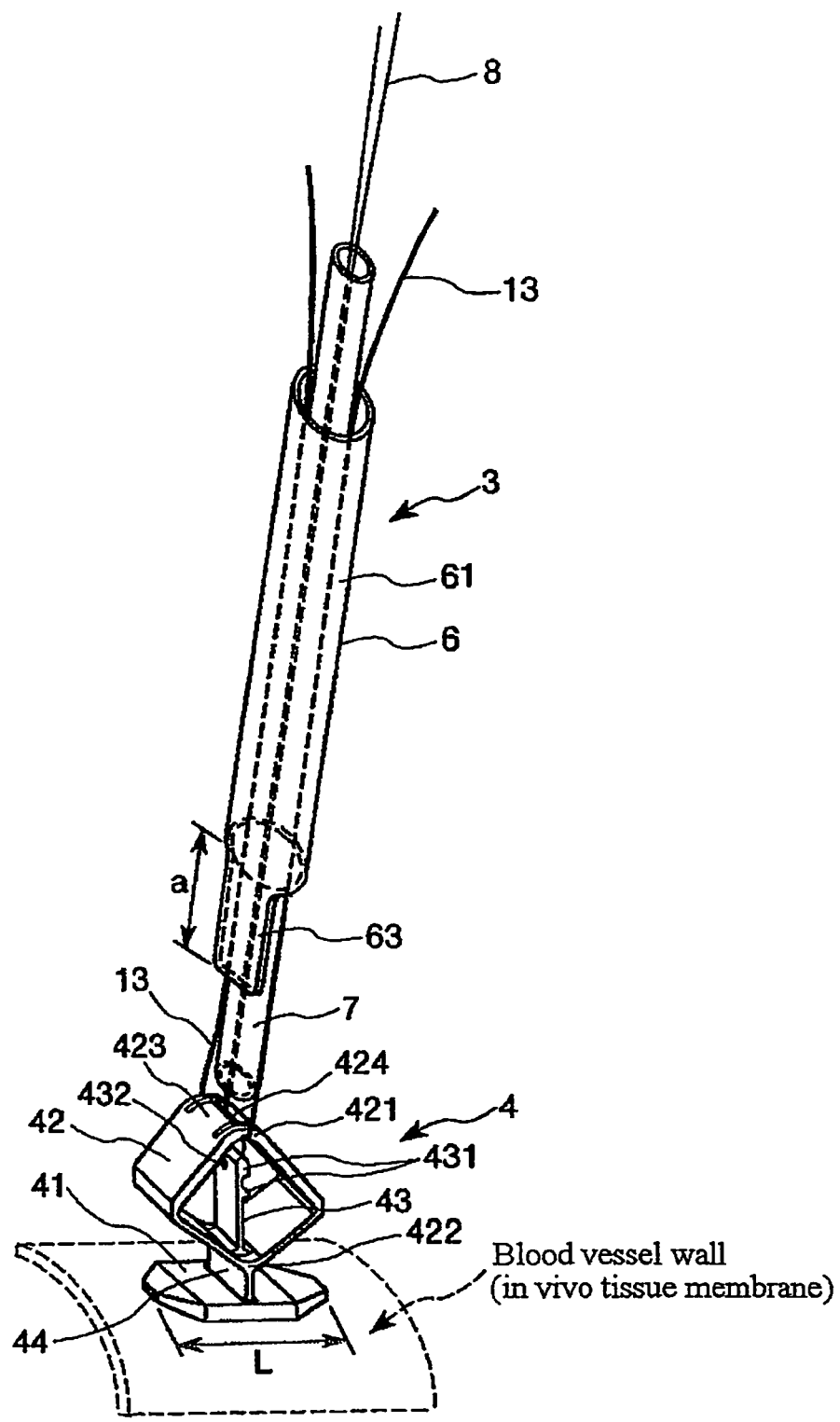

FIG. 18 is a perspective view of a third embodiment of a tissue closing device described herein.

FIGS. 19(a)-(c) are perspective views illustrating various operational aspects of the tissue closing device shown in FIG. 18.

FIGS. 20(a)-(c) are perspective views illustrating other operational aspects of the tissue closing device shown in FIG. 18.

Figure 21:
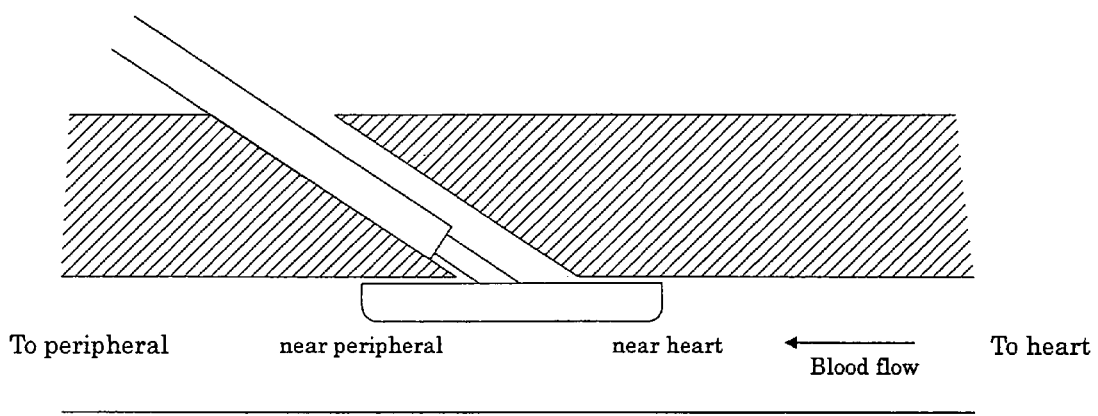

FIG. 21 is a schematic illustration for explanatory purposes showing tissue closing device positioned in an artery.

DETAILED DESCRIPTION

A first embodiment of the living body tissue closing device disclosed herein will be described below with reference to FIGS. 1-12. For purposes of convenience in description, in FIGS. 1 and 6-11, the left lower side is referred to as the "distal end" and the right upper side is referred to as the "proximal end". Further, in FIGS. 2-5 and 12, although the upper side of the living body tissue closing device as a whole in these figures is the "proximal end" and the lower side is the "distal end", as regards the clip (living body tissue closure) 4, the upper side in the drawing figures is referred to as the "distal end" and the lower side is referred to as the "proximal end".

The living body tissue closing device 1 is a device for closing a transdermally penetrating wound hole (opening which penetrates a living body tissue membrane) which is formed, for example, in a living organism lumen such as a blood vessel, an internal organ of a living organism or a living body tissue membrane such as an internal tissue of a living organism.

Figure 7:
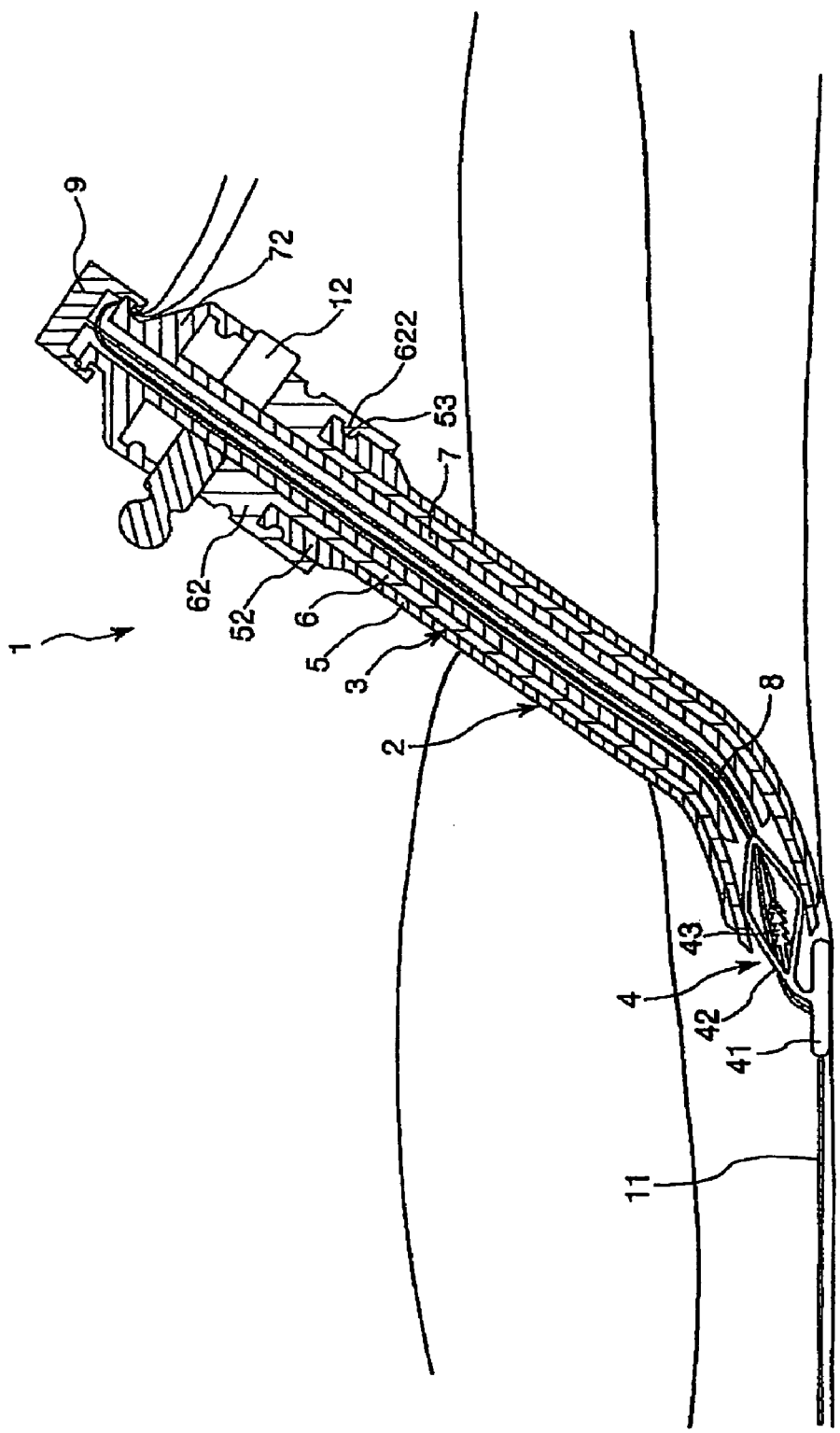
FIG. 7 is a cross-sectional view illustrating another operational aspect of the tissue closing device shown in FIG. 1.
Figure 8:
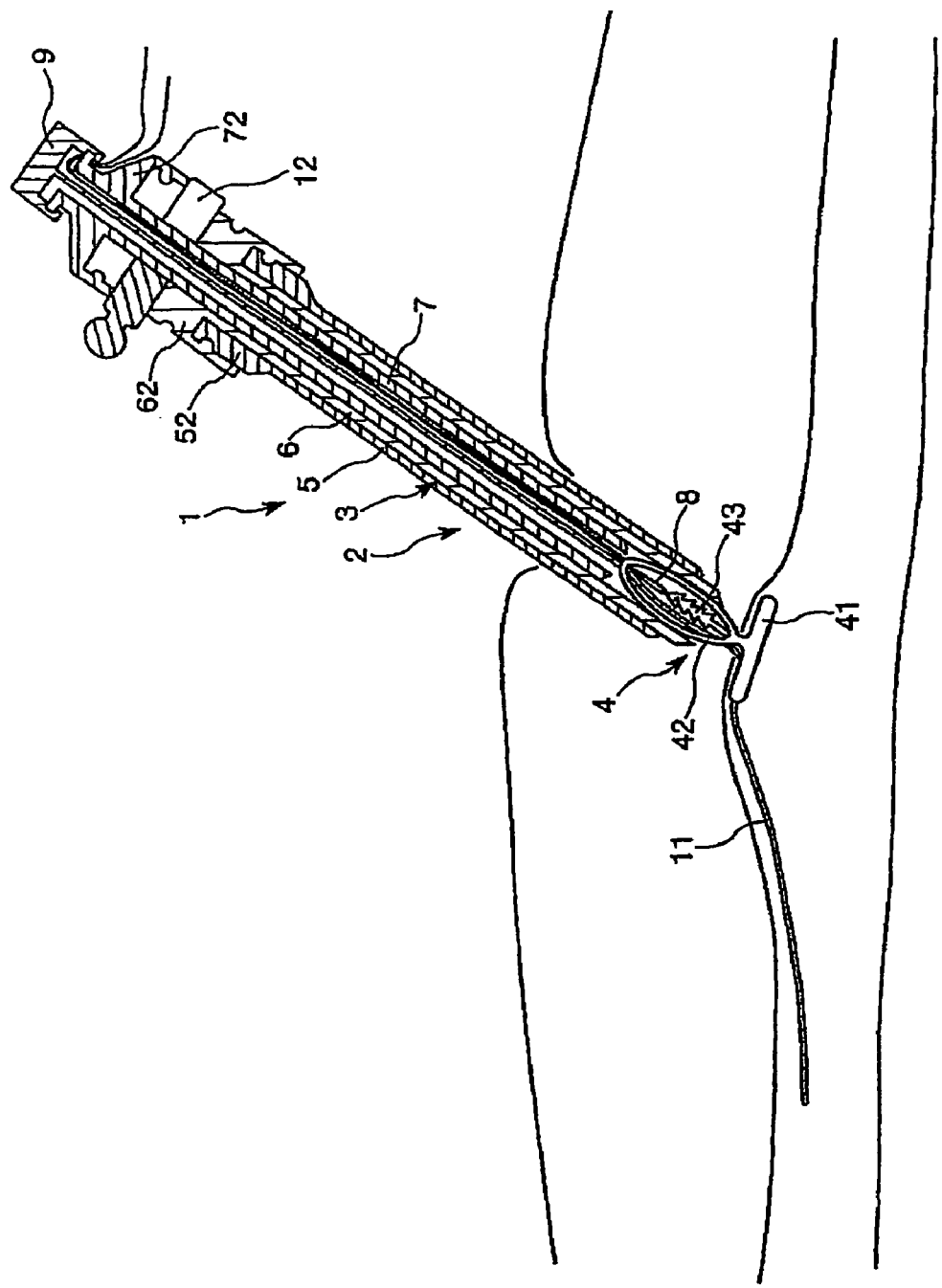
FIG. 8 is a sectional view illustrating another operational aspect of the tissue closing device shown in FIG. 1.

As shown in FIGS. 7 and 8, the living body tissue closing device 1 includes an elongated body element 2, and a clip 4 movably located at the distal end portion of the body element 2 and serving as a living body tissue closure (closing up section) for closing a wound hole penetrating a living body tissue membrane. The living body tissue closing device 1 further includes a thread (thread-like member or string member) 8 serving as pulling means for pulling the clip 4.

Figure 1:
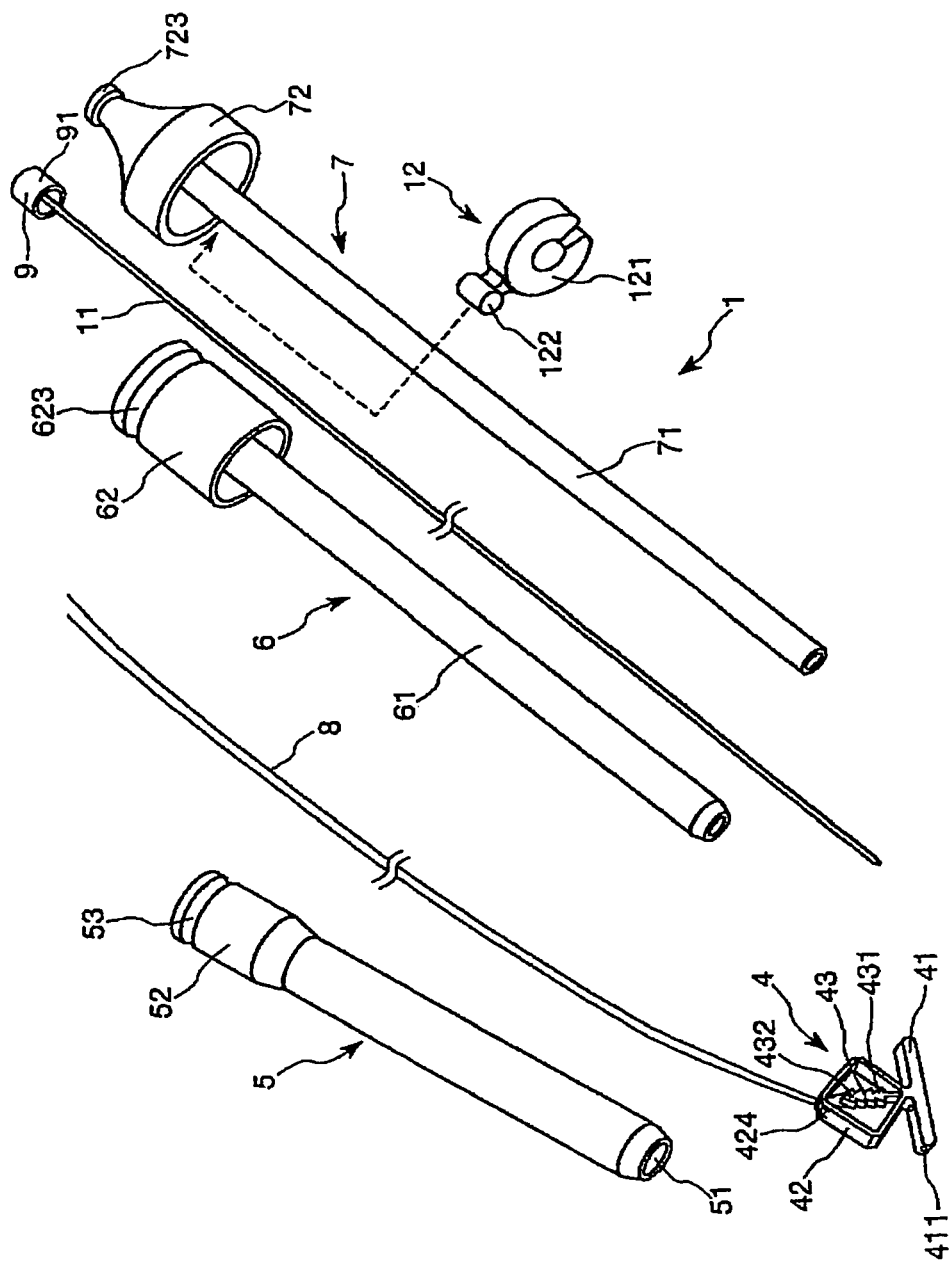
Figure 3:
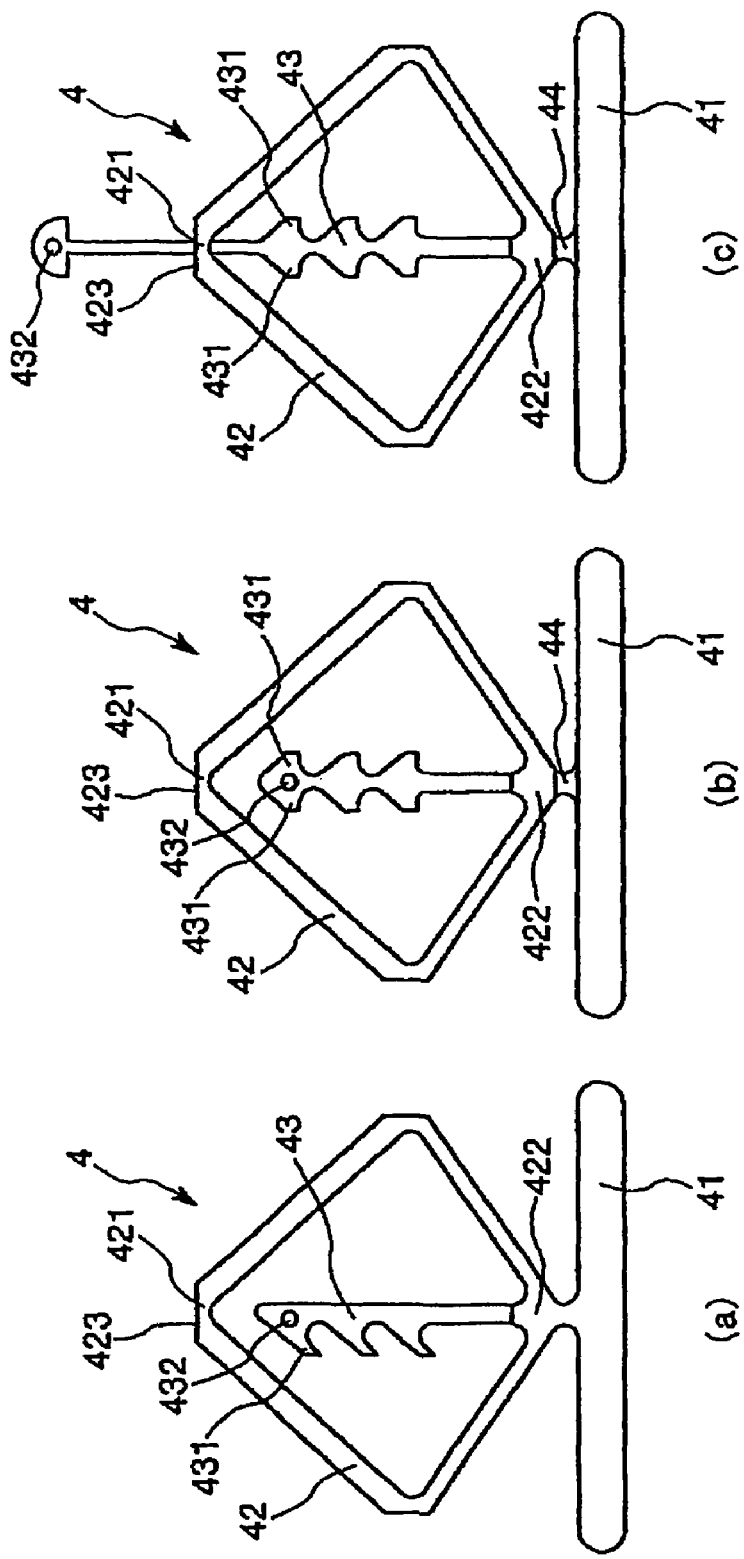
Figure 6:
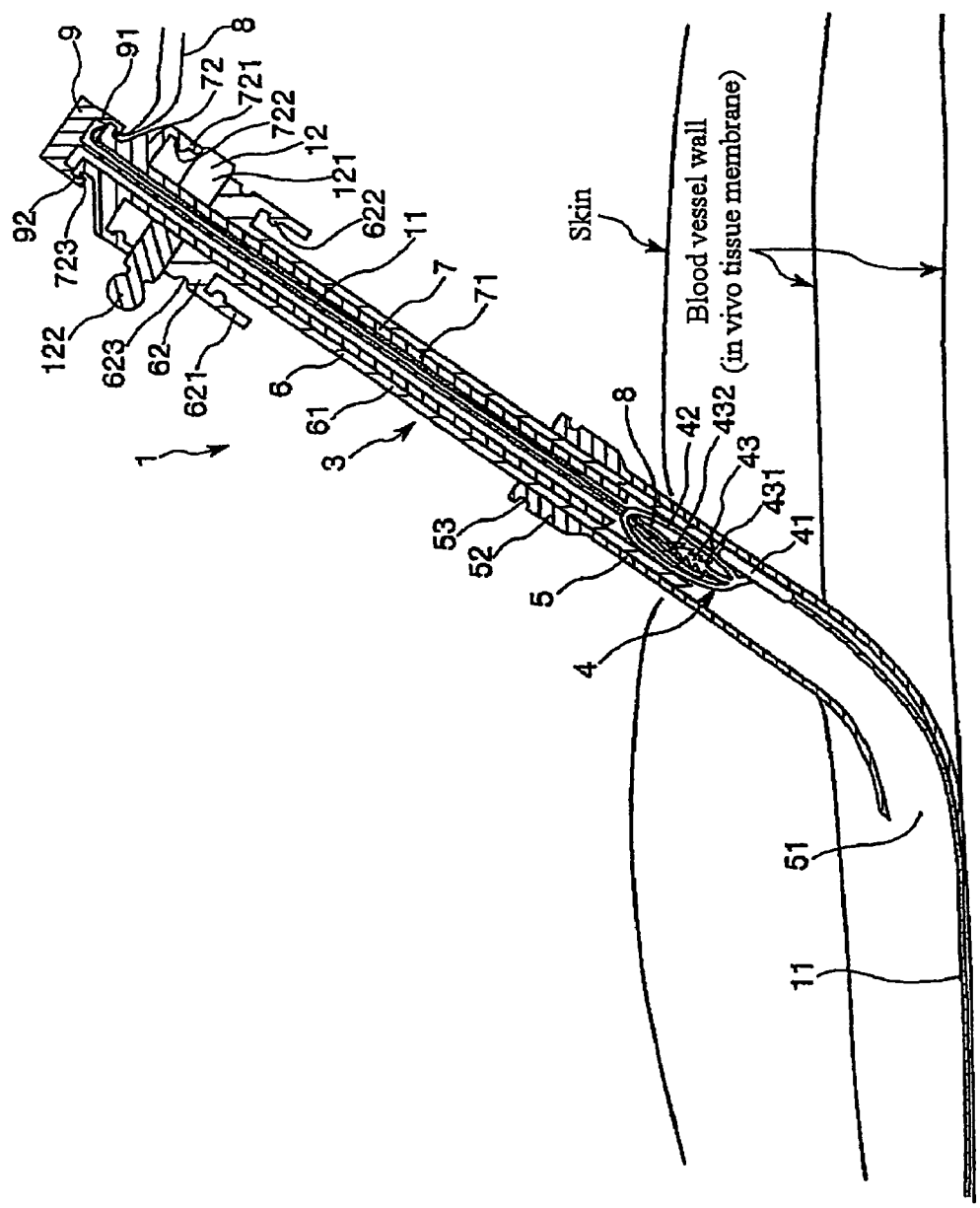
FIG. 6 is a cross-sectional view illustrating on operational aspect of the tissue closing device shown in FIG. 1.

As shown in FIGS. 1, 6 and 7, the body element 2 includes a sheath 5 having a through-hole 51 extending through a central portion thereof in the axial direction, and an elongated feeding and deformation means (delivery device) 3 removably mounted on the sheath 5. During a staunching operation (operation of closing a wound hole), the distal end portions of the sheath 5, the feeding and deformation means 3 and the clip 4 individually penetrate the wound hole. In other words, they are inserted into a lumen (living organism lumen) of a living organism such as a blood vessel through the wound hole.

The sheath 5 has a substantially cylindrical shape and has a hub 52 at the proximal end portion thereof. A circumferentially expending groove 53 is provided on the outer periphery of the hub 52 near the proximal end.

For the sheath 5, a sheath (introducer sheath) dwelling after treatment (PCI) is performed using a catheter or after treatment of a diagnosis (CAG) may be used. Alternatively, a sheath for exclusive use with the living body tissue closing device 1 may be used.

The description above describes the sheath 5 as a component of the body element 2. However, the sheath 5 need not be included in components of the body element 2.

The feeding and deformation means 3 includes a covered tube (tubular member) 6, a pusher tube (tubular member) 7, a thread anchoring cap (thread retaining member) 9, a guide wire 11 having one end secured to the thread anchoring cap 9, and a stopper 12. The covered tube 6 and the pusher tube 7 constitute parts that assist in feeding the clip 4 and pressing a deformation portion 42 of the clip 4 (described in more detail below) to deform the deformation portion 42 into a second form.

The covered tube 6 includes a tube body 61 and a hub 62 provided at the proximal end portion of the tube body 61. The hub 62 has a cylindrical tubular portion 621. The clip 4 is removably located (retained) at the distal end portion of the covered tube 6. In this instance, the clip 4 is mounted such that the deformation portion 42 of the clip is retained in a lumen at the distal end portion of the covered tube 6.

An inwardly directed circumferentially extending rib 622 is formed on an inner circumferential face of the tubular portion 621. This rib 622 is adapted to engage the groove 53 formed on the hub 52 of the sheath 5. Further, a circumferentially extending groove 623 is formed on the outer circumferential face of the hub 62.

The inner diameter of the tubular portion 621 of the hub 62 is a little greater than the outer diameter of the hub 52 of the sheath 5, and the outer diameter of the tube body 61 is a little smaller than the inner diameter of the sheath 5. Consequently, the tube body 61 of the covered tube 6 can be inserted into the sheath 5 while the hub 52 of the sheath 5 can be inserted into the tubular portion 621 of the hub 62 of the covered tube 6, with the rib 622 of the hub 62 engaging the groove 53 of the hub 52. Where the rib 622 is engaged with the groove 53, one of the sheath 5 and the covered tube 6 is blocked from coming off the other, and this facilitates operation.

The pusher tube 7 includes a tube body 71 and a hub 72 provided at the proximal end portion of the tube body 71. The hub 72 has a cylindrical tubular portion 721. The pusher tube 7 is adapted to push out the clip 4, disposed at the distal end portion of the covered tube 6, from the covered tube 6 so as to be released from the covered tube 6.

A circumferentially extending rib 722 is formed on the inner circumferential face of the tubular portion 721. This rib 722 is adapted to engage the groove 623 formed on the tube body 61 of the covered tube 6.

The outer diameter of the distal end portion of the hub 72 is smaller than the outer diameter of the tubular portion 721. A circumferentially extending rib (flange) 723 is formed on the outer circumferential face of the hub 72 at the proximal end of the hub 72.

The inner diameter of the tubular portion 721 of the hub 72 is a little greater than the outer diameter of the hub 62 of the covered tube 6, and the outer diameter of the tube body 71 is a little smaller than the inner diameter of the covered tube 6. Consequently, the tube body 71 of the pusher tube 7 can be inserted into the covered tube 6 while the hub 62 of the covered tube 6 can be inserted into the tubular portion 721 of the hub 72 of the pusher tube 7, with the rib 722 of the hub 72 engaging the groove 623 of the hub 62. With the rib 722 engaged with the groove 623, the possibility that one of the covered tube 6 and the pusher tube 7 will separate (come out from) from the other is blocked, and this facilitates operation.

The thread anchoring cap 9 is removably mounted on the hub 72 of the pusher tube 7 and possesses a cylindrical tubular portion 91. A circumferentially extending groove 92 adapted to engage the rib 723 formed on the hub 72 of the pusher tube 7 is formed on the inner circumferential face of the tubular portion 91.

One end of the guide wire 11 is secured in the tubular portion 91 of the thread anchoring cap 9.

When the thread 8 is disposed between the thread anchoring cap 9 and the hub 72 of the pusher tube 7, and the thread anchoring cap 9 is mounted on the hub 72 until the rib 723 is engaged with the groove 92, the possibility that the thread anchoring cap 9 will come out from or be separated from the hub 72 of the pusher tube 7 is inhibited or prevented, and the thread 8 is sandwiched between and retained by the tubular portion 91 of the thread anchoring cap 9 and the rib 723 of the hub 72.

The stopper 12 is removably mounted on the tube body 71 of the pusher tube 7. The stopper 12 includes a substantially C-shaped attaching portion 121 and a gripping portion 122.

The stopper 12 is mounted on the tube body 71 in the proximity of the hub 72 by fitting the tube body 71 of the pusher tube 7 into the attaching portion 121. The stopper 12 is mounted on the tube body 71 at a position generally indicated by the broken line in FIG. 1.

As shown in FIGS. 1 and 2, the clip (living body tissue closure) 4 includes a seal portion 41, a deformation portion or sustaining portion 42 deformable between a first form and a second form, and a fastener or retaining portion 43 for retaining the deformation portion 42 in the second form. Preferably, the seal portion 41, the deformation portion 42 and the fastener portion 43 are formed integrally in one piece from the same material.

The seal portion 41 is a member having a flat face portion (flat face) for covering a wound hole and a surrounding portion of the wound hole (the portion of a living body tissue membrane including the wound hole) from one side (inner surface) of the living body tissue membrane. In the illustrated embodiment, the seal portion 41 is plate-shaped so that it possesses a substantially rectangular shape as viewed in plan.

The deformation portion 42 is frame-shaped and is adapted to be deformed from a basic or initial form (shape) to a first form in which it can pass through a wound hole and to a second form in which it cooperates with the seal portion 41 to sandwich the living body tissue membrane therebetween to sustain the seal portion on one side of the living body tissue membrane. The deformation portion 42 thus cooperates with the seal portion 41 so that the living body tissue membrane is sandwiched or positioned between the seal portion 42 and the deformation portion 42, with the seal portion 41 positioned on one side (the inner surface side) of the living body tissue membrane and the deformation portion 42 positioned on the other side (outer surface side) of the living body tissue membrane to retain or hold the seal portion 41 to the one side of the living body tissue membrane. Accordingly, the deformation portion 42 forms a retainer which cooperates with the seal portion 41 positioned on one side of the living body tissue membrane to sandwich the living body tissue membrane therebetween from the other side of the living body tissue membrane to retain the seal portion to the one side. Where the living body tissue membrane is a blood vessel wall (living organism lumen wall), the one side at which the seal portion 41 is positioned is the inner surface of the blood vessel wall (living organism lumen wall) while the other side at which the deformation portion 42 is positioned is the outer surface of the blood vessel wall (living organism lumen wall).

Here, in the present embodiment, the deformation portion 42 has a quadrangular shape (quadrangular framework) like a pantograph formed from four links connected integrally to each other. With respect to the two diagonally oppositely located corner portions 421, 422 at the upper and lower positions in FIG. 2, the lower side corner portion 422 (on the seal portion 41 side) in FIG. 2 is connected to the seal portion 41 and serves as a fixed portion which cannot move relative to the seal portion 41 or the fastener portion 43. Consequently, when the deformation portion 42 is deformed, the diagonally opposite corner portions 421, 422 move toward and away from each other.

Accordingly, the deformation portion 42 can be deformed to expand or contract in two directions perpendicular to each other, and can also rock (pivot) with respect to the seal portion 41 (turn around one axis of turning motion) as the four corner portions (corner) bend like articulations. In other words, the seal portion 41 can rock (turn around one axis of turning motion) with respect to the deformation portion 42. In this instance, the connecting portion between the seal portion 41 and the corner portion 422 of the deformation portion 42 is flexible, and as the connecting portion bends (is elastically deformed), the seal portion 41 turns.

Further, the upper face (surface on the opposite side to the seal portion 41) of the corner portion 421 on the upper side in FIG. 2 (on the opposite side to the seal portion 41) exhibits a substantially flat face or surface.

A substantially H-shaped slit 424 is formed in the corner portion 421 as shown in FIG. 2(c). The slit 424 forms an opening extending through the framework-shaped deformation portion 42. At least part of the fastener portion 43 can be inserted, fitted or received in the corner portion 421 by way of the slit 424.

The fastener portion 43 possesses a bar-like shape. The fastener portion 43 is positioned within the interior of the framework defined by the plural sides of the deformation portion 42 and is connected at its proximal end portion (lower side end portion in FIG. 2(a)) to the inner surface of the corner portion 422 so that the fastener portion 43 is connected to the seal portion 41 via the corner portion 422.

Consequently, the fastener portion 43 can rock (turn or pivot about a single axis of turning/pivoting motion) together with the deformation portion 42 with respect to the seal portion 41. In other words, the seal portion 41 is able to pivot or turn with respect to the deformation portion 42 and the fastener portion 43 about a single axis (i.e., the relative pivoting/turning movement between the seal portion 41 on the one hand and the deformation portion 42 and fastener portion 43 on the other hand is limited to pivoting/turning movement in a single plane).

A number of pawls 431 (four in the illustrated example) are formed on opposite sides or surfaces of the fastener portion 43 in the leftward and rightward direction relative to the illustration in FIG. 2(a). The pawls 431 are juxtaposed in a spaced relationship by a predetermined distance from each other in the longitudinal direction of the fastener portion 43 (upward and downward direction in FIG. 2a)).

If the above-described feeding and deformation means 3 (body element 2) is moved in a direction toward the distal end thereof, the distal end portions of the covered tube 6 and the pusher tube 7 are brought into contact with the upper face 423 of the corner portion 421 of the deformation portion 42 or with a part of the deformation portion 42 around the upper face 423 at the upper side in FIG. 2(a). Thus, the corner portion 421 of the deformation portion 42 is pressed toward the lower side in FIG. 2(a) (i.e., toward the corner portion 422) by the covered tube 6 and the pusher tube 7. At this time, the fastener portion 43 is positioned within the pusher tube 7 and does not present an obstacle (such as shown in FIG. 10).

Figure 10:
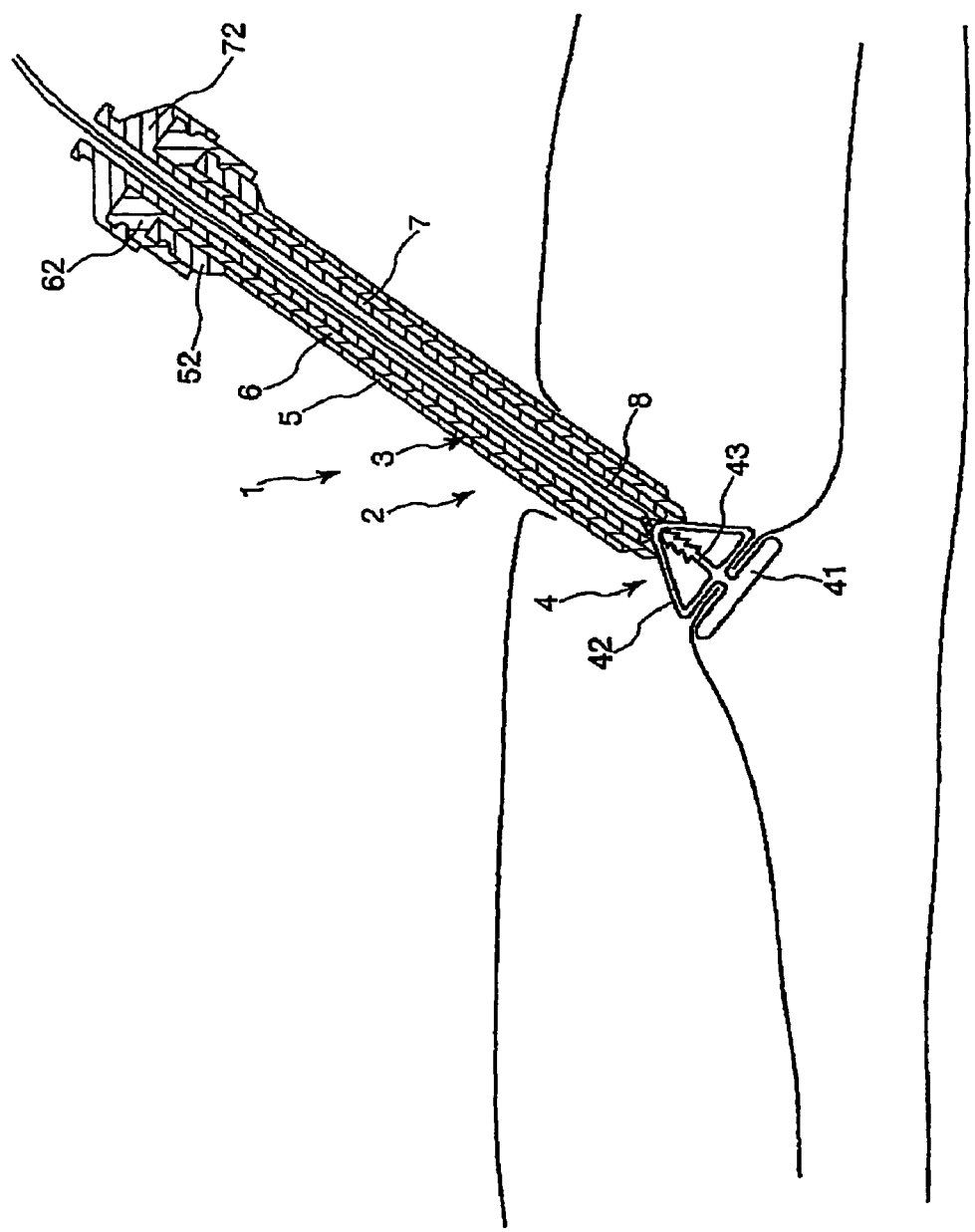
FIG. 10 is a sectional view illustrating a further operational aspect of the tissue closing device shown in FIG. 1.

As the corner portion 421 of the deformation portion 42 moves to the lower side in FIG. 2(a), the upper side end portion of the fastener portion 43 in FIG. 2(a) and the uppermost ones of the pawls 431 of the fastener portion 43 in FIG. 2(a) pass through the slit 424 formed in the corner portion 421 and are brought into engagement with the corner portion 421 as generally illustrated in FIG. 10.

If the pushing force applied by the covered tube 6 and the pusher tube 7 is canceled in this state, the shape of the deformation portion 42 is maintained by the engagement between the pawls 431 and the corner portion 421. Further, even if the corner portion 421 of the deformation portion 42 is pushed in the upper direction in FIG. 2(a), the shape of the deformation portion 42 is maintained.

It is to be noted that, as described in more detail below, the operation described above is performed while the fastener portion 43 of the clip 4 is being pulled by the thread 8.

Figure 11:
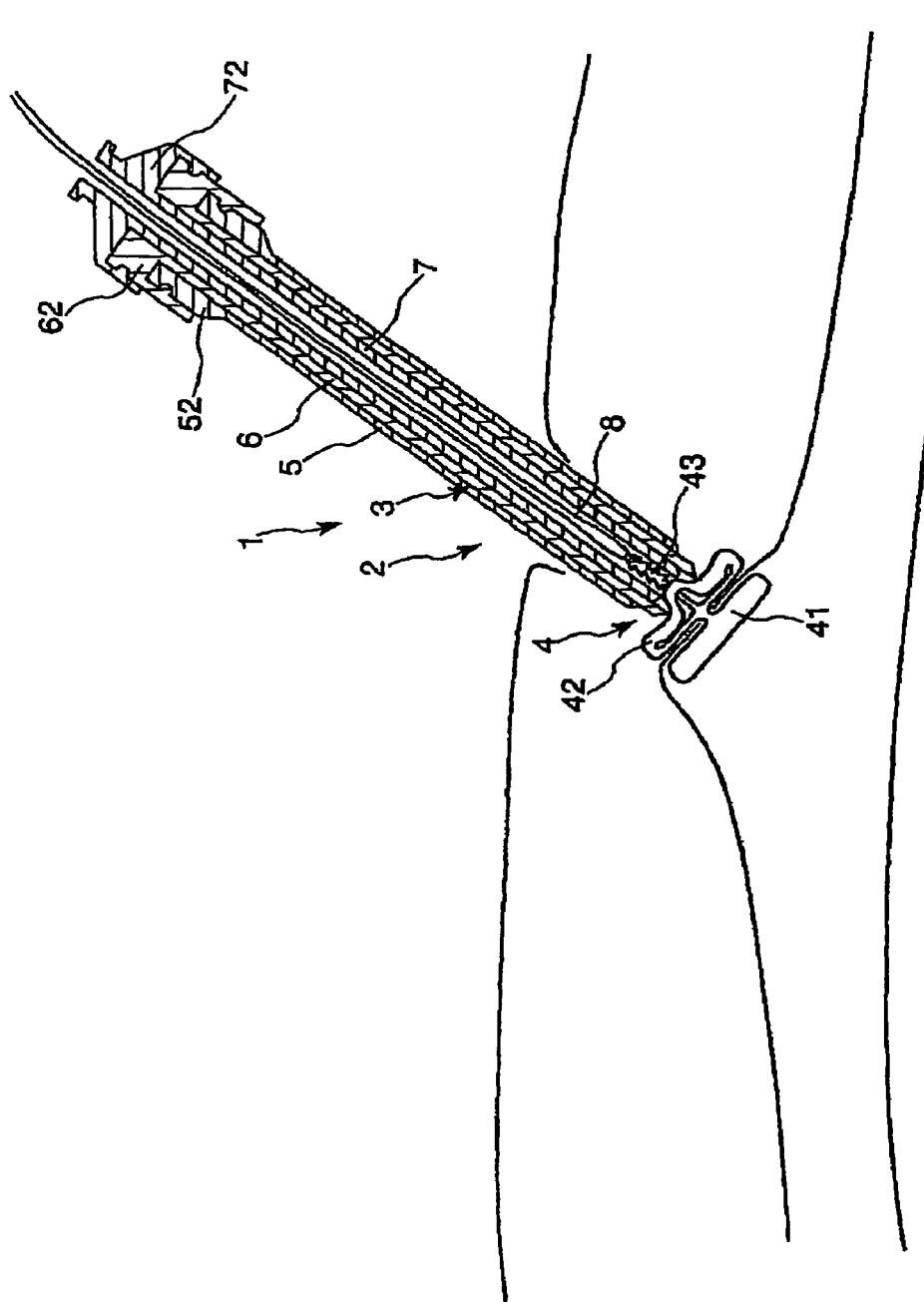
FIG. 11 is a sectional view illustrating yet another operational aspect of the tissue closing device shown in FIG. 1.
Figure 12:
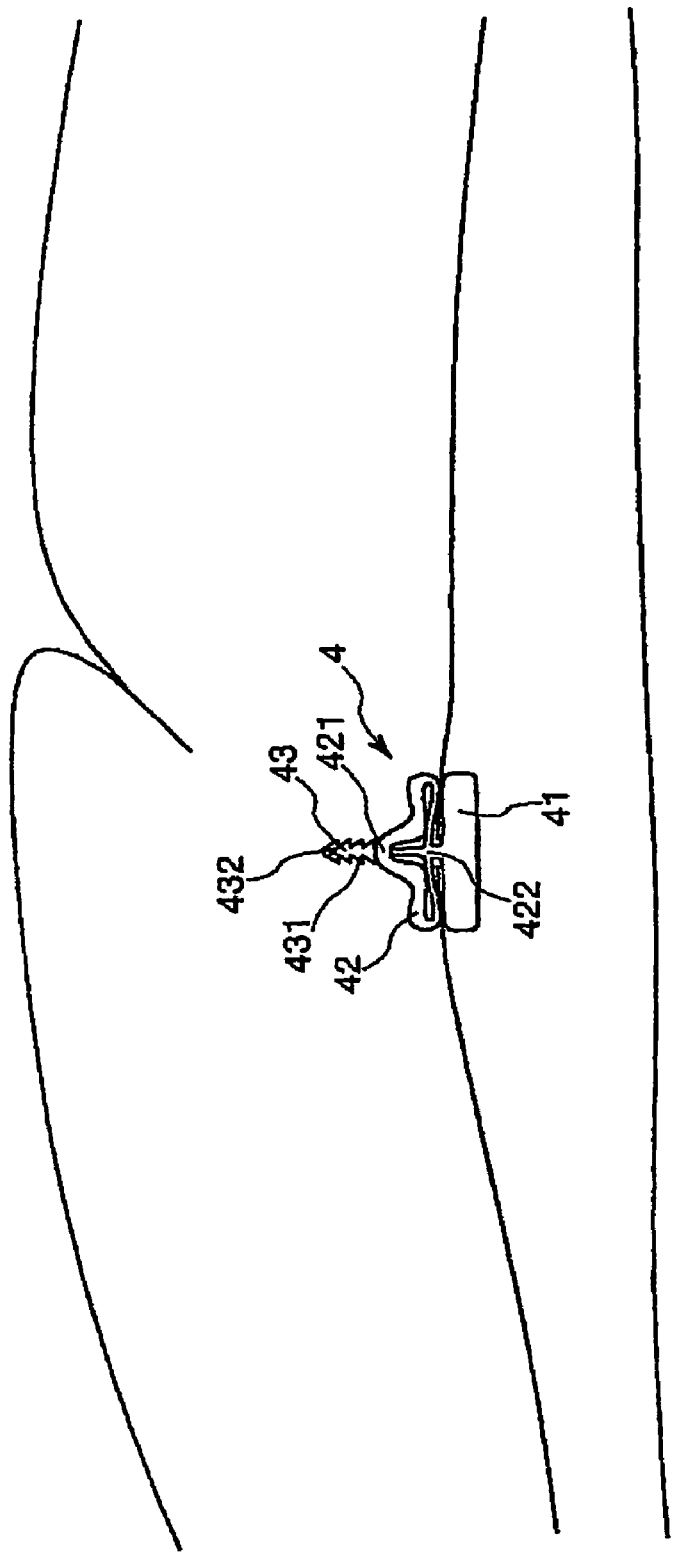
FIG. 12 is a sectional view illustrating another operational aspect of the tissue closing device shown in FIG. 1.

If the feeding and deformation means 3 (body element 2) is further moved in the direction toward the distal end thereof, the corner portion 421 of the deformation portion 42 is further pressed to the lower side in the downward direction in FIG. 2(a) by the covered tube 6 and the pusher tube 7. Consequently, the corner portion 421 of the deformation portion 42 further moves to the lower side in the downward direction in FIG. 2(a) while the pawls 431 of the fastener portion 43 successively pass through the slit 424 in the corner portion 421, until the lowermost ones of the pawls 431 in FIG. 2(a) are fully engaged with the corner portion 421 as generally shown in FIGS. 11 and 12.

As mentioned above, even if the pushing force applied by the covered tube 6 and the pusher tube 7 is cancelled in this state, and even if the corner portion 421 of the deformation portion 42 is pushed to the upper side in the upward direction in FIG. 2(a), the shape of the deformation portion 42 is maintained. This similarly applies also to an intermediate stage of deformation.

In this manner, the deformation portion 42 is deformed such that the corner portion 421 and the corner portion 422 approach each other, or are positioned closer to one another compared to the basic state, to establish the second form of the clip 4 in which the deformation portion 42 cooperates with the seal portion 41 to sandwich a living body tissue membrane therebetween to close a wound hole, with the pawls 431 engaged with the corner portion 421 to maintain this second form.

In the second form of the deformation portion 42, deformation of the deformation portion 42 in a direction in which the degree of deformation of the deformation portion 42 decreases is inhibited or blocked by the fastener portion 43, while deformation in the other direction in which the degree of deformation of the deformation portion 42 increases is permitted. Thus, the degree of deformation of the deformation portion 42 can be controlled or adjusted to a plurality of stages. In particular, in the second form of the deformation portion 42, deformation of the deformation portion 42 in the direction in which the corner portion 421 and the corner portion 422 are moved away from each other is inhibited or blocked by the fastener portion 43, whereas deformation of the deformation portion 42 in the other direction in which the corner portion 421 and the corner portion 422 move toward each other is permitted, and the distance between the two corner portions 421, 422 can be controlled or adjusted to a plurality of stages. Consequently, the living body tissue closing device 1 has useful application in a variety of different conditions and under a variety of different circumstances such. For example, the device can be sued with a person who has a thick living body tissue membrane, a person who has a thin living body tissue membrane, a person who has a hard living body tissue membrane, and a person who has a soft living body tissue membrane.

A hole (through-hole) 432 through which the thread 8 is to be threaded is formed at the distal end portion of the fastener portion 43. As shown in FIGS. 1 and 6, the thread 8 passes through the slit 424 of the corner portion 421 of the deformation portion 42 from the upper side in FIG. 1, through the hole 432 of the fastener portion 43 and further through the slit 424 from the lower side in FIG. 1.

In this state, the opposite end portions of the thread 8 are threaded through the inside of the pusher tube 7 and pulled out to the outside from the proximal end portion of the pusher tube 7. In this state, the thread anchoring cap 9 is then mounted on the hub 72, whereupon the opposite end portions of the thread 8 are sandwiched (retained) between the thread anchoring cap 9 and the hub 72, whereby the opposite end portions of the thread 8 can be retained at the proximal end portion of the pusher tube 7. In other words, the thread 8 has the fastener portion 43 retained at an end portion thereof, and in this state the thread 8 is retained at the other end portion thereof to the proximal end portion of the pusher tube 7.

As shown in FIGS. 1 and 2, a hole (through-hole) 425 through which the guide wire 11 is to be passed is formed in the deformation portion 42 in the proximity of the corner portion 422. Further, a hole (through-hole) 411 through which the guide wire 11 is to be passed is formed in the seal portion 41. The hole 411 opens at one end to the left side end portion of the seal portion 41 in FIG. 2(b) and opens at the other end at the upper surface of the seal portion 41 in FIG. 2(b) in proximity to the hole 425.

As shown in FIG. 6, the guide wire 11 passes through the slit 424 at the corner portion 421 of the deformation portion 42, passes through the hole 425 in the deformation portion 42 and passes through the hole 411 in the seal portion 41.

At least a part of the clip 4 is preferably formed from a bioabsorbable material. Preferably, the entire clip 4 is formed from a bioabsorbable material. In this instance, since the clip 4 is absorbed by a living organism after a predetermined interval of time and does not finally remain in the living organism, an influence on the human body can be eliminated.

Examples of bioabsorbable material to be used for the clip 4 include a simple substance of polylactic acid, polyglycolic acid, or polydioxanon or a complex of them.

It is to be noted that, as a component material of the clip 4, not only a bioabsorbable material but also a biocompatible material such as a resin or a metal can be used.

Further, the clip 4 is preferably made of a material having quite good hinge characteristics as a physical property required particularly for the deformation function of the deformation portion 42. More specifically, a material having a tensile strength of 100 to 500 ($Kg/cm^2$), an elongation of 50 to 800% and a tensile modulus of 5 to 25 ($\times 10^3$ $Kg/cm^2$) is preferably used.

Where the physical property values specified are satisfied, the clip 4 is quite good in hinge characteristics and the deformation portion 42 has a desired deformation capability.

The seal portion 41 and the deformation portion 42 which are components of the clip 4 are preferably formed integrally from the bioabsorbable material described above. Also, the fastener portion 43 is preferably formed integrally from the same material as that of the seal portion 41 and the deformation portion 42.

Further, a lubricating surface treat member such as silicon coating is applied to the outer surface of the clip 4 formed from the bioabsorbable material to reduce the resistance of the clip 4 upon insertion into a living organism so as to facilitate arrangement of the clip 4 into a living organism. Further, if an X-ray contrast agent is mixed into a material for forming the clip 4 or is coated on the surface of the clip 4, when the clip 4 is disposed into a living organism, the position of the clip 4 can be observed or otherwise determined under an X-ray image.

It is to be noted that the clip 4 used in the disclosed device is not limited to the clip 4 having the configuration described above. Examples of other configurations of the clip are shown in FIGS. 3(a)-(c), FIGS. 4(a) and 4 (b) and FIG. 5. The following description of these alternatives addresses primarily the differences relative to the clip 4 described above and shown in FIG. 2. A detailed description of the features associated with these alternative configurations for the clip that are the same as those already described is not repeated.

In the clip 4 shown in FIG. 3(a), the pawls 431 are formed on only one side (only on the left side in FIG. 3(a)) of the fastener portion 43.

In the clip 4 shown in FIG. 3(b), the width of the connecting portion 44 (length in the direction perpendicular to the plane of the figure) between the seal portion 41 and the deformation portion 42 (fastener portion 43) is narrower (shorter) than that of the clip 4 described above with reference to FIG. 2.

In the clip 4 shown in FIG. 3(c), the length of the fastener portion 43 in the longitudinal direction is longer than the clip 4 described above with reference to FIG. 2, and the distal end portion of the fastener portion 43 extends through the slit 424 of the corner portion 421 of the deformation portion 42.

Further, the width of the connecting portion 44 (length in the direction perpendicular to the plane of the figure) between the seal portion 41 and the deformation portion 42 (fastener portion 43) is narrower (shorter) than the clip 4 described above with reference to FIG. 2.

In the clip 4 shown in FIG. 4(a), projections 428, 429 are formed at two corner portions 426, 427 positioned at the diagonal positions in the leftward and rightward direction in FIG. 4(a), respectively. The projection 428 extends along an extension line of a left upper link (side) in FIG. 4(a) forming the deformation portion 42, and the projection 429 extends along an extension line of a right upper link (side) in FIG. 4(a) forming the deformation portion 42.

When a living body tissue membrane is sandwiched between the deformation portion 42 and the seal portion 41, the subcutaneous tissues can be collected in the proximity of the wound hole by the projections 428, 429. Consequently, the wound hole can be closed up with a relatively high degree of certainty.

In the clip 4 shown in FIG. 4(b), the pawls 431 are formed on the opposite sides of the fastener portion 43 in the direction perpendicular to the plane of FIG. 4(b). In other words, the positions of the pawls 431 of the fastener portion 43 are displaced 90° with respect to the positioning of the pawls in the clip 4 described above with reference to FIG. 2.

Further, the width of the connecting portion 44 (length in the direction perpendicular to the plane of the figure) between the seal portion 41 and the deformation portion 42 (fastener portion 43) is narrower (shorter) than the clip 4 described above with reference to FIG. 2.

Figure 5:
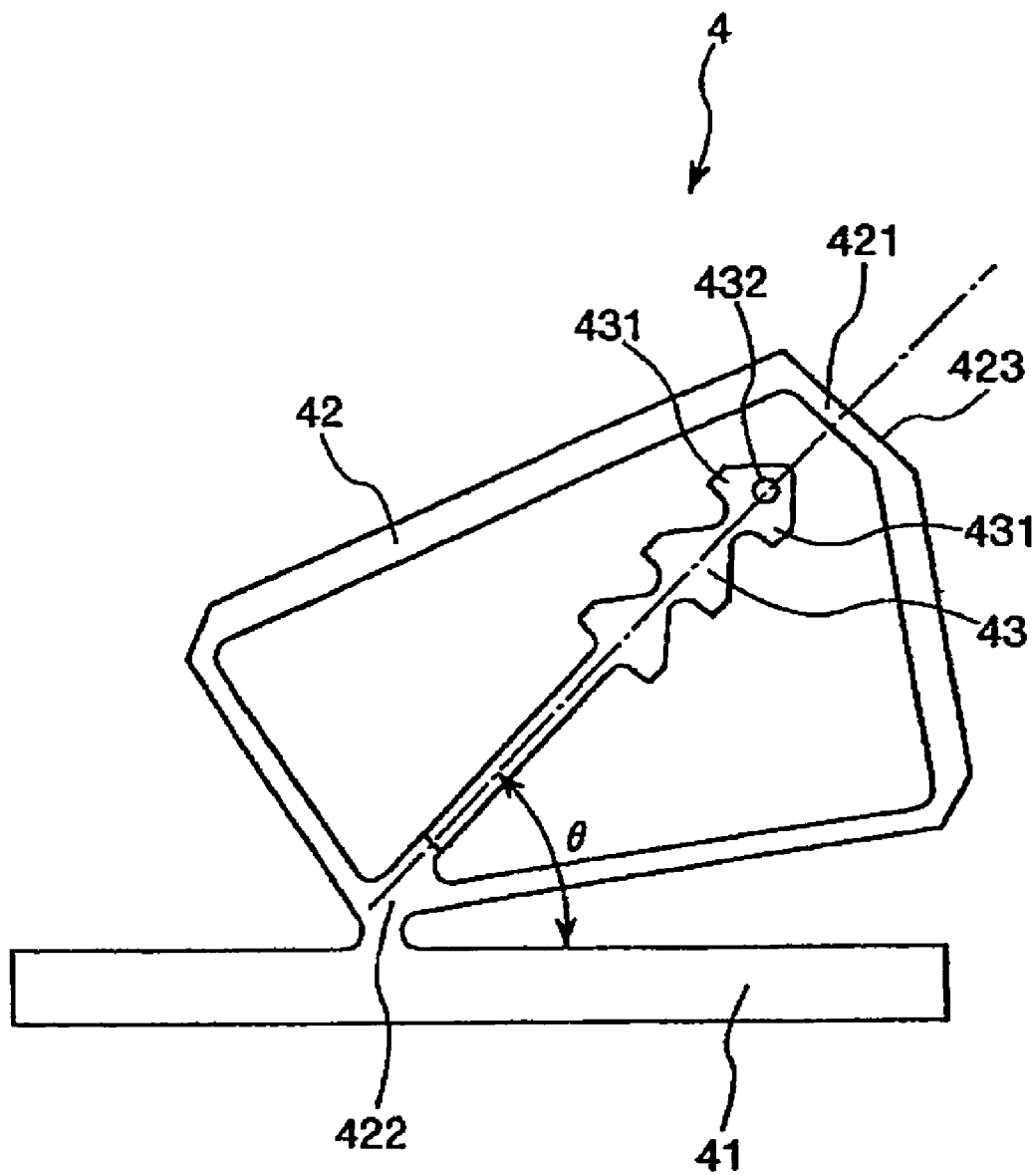
FIG. 5 is a side elevational view showing a still further example of a configuration of the tissue closure of the tissue closing device shown in FIG. 1.

In the clip 4 shown in FIG. 5, in its basic form (basic shape), the fastener portion 43 and the deformation portion 42 are inclined with respect to the seal portion 41.

In particular, since the body element 2 is inserted in an inclined relationship, for example, into a blood vessel by a predetermined angle with respect to the seal portion 41, the fastener portion 43 and the deformation portion 42 are inclined with respect to the seal portion 41 in a corresponding relationship. In this instance, preferably the fastener portion 43 and the deformation portion 42 are inclined with respect to the seal portion 41 to such a degree that, when the direction of the blood vessel and the direction of the major side (longitudinal direction) coincide with each other, the longitudinal direction of the body element 2 and the direction of the center axis of the fastener portion 43 substantially coincide with each other.

More particularly, the angle (inclination angle) θ defined by the center axis of the fastener portion 43 and the surface of the seal portion 41 on the deformation portion 42 side (the plane in which the surface of the seal portion 41 lies) is preferably set to a predetermined value within a range of 30° to 60°. Thus, the wound hole can be closed with a relatively high degree of certainty.

It is to be noted that the shape of the deformation portion of the clip (living body tissue closure) is not limited to a quadrangular shape but may be some other polygon in the shape of a framework, or may be in the shape of a framework having no angle such as an annular framework or an elliptic framework. Further, the shape of the deformation portion may be a shape different than that in the shape of a framework.

Further, in the clip described above, the number of pawls at the fastener portion of the clip (living body tissue closure) may be only one.

A procedure for performing a staunching operation (operation of the living body tissue closing device 1) using the living body tissue closing device 1 is described below.

First, the feeding and deformation means 3 is assembled in the manner shown FIG. 6. The stopper 12 is first mounted on the tube body 71 of the pusher tube 7 (e.g., at a position indicated by the broken line in FIG. 1), and then the pusher tube 7 is inserted into the covered tube 6 from the proximal end side of the covered tube 6. The stopper 12 is then positioned between the hub 72 of the pusher tube 7 and the hub 62 of the covered tube 6.

In addition, as shown in FIG. 1, the thread 8 is threaded into the slit 424 of the deformation portion 42 of the clip 4 from the upper side in FIG. 1, is threaded through the hole 432 of the fastener portion 43, and is further threaded through the slit 424 from the lower side in FIG. 1.

Further, as shown in FIG. 6, the guide wire 11 is inserted into the pusher tube 7 from the proximal end side of the pusher tube 7 and is passed through the slit 424 of the deformation portion 42 of the clip 4, the hole 425 of the deformation portion 42 and the hole 411 of the seal portion 41.

Then, the opposite end portions of the thread 8 are inserted into the pusher tube 7 from the distal end side of the pusher tube 7 and drawn out from the proximal end portion of the pusher tube 7.

Further, the deformation portion 42 of the clip 4 is deformed, and the deformed deformation portion 42 is inserted into (mounted at) the covered tube 6 from the distal end side of the covered tube 6.

Then, in this state, the thread anchoring cap 9 is mounted on the hub 72 of the pusher tube 7, and the rib 723 of the hub 72 is engaged with the groove 92 of the thread anchoring cap 9. Consequently, the opposite end portions of the thread 8 are sandwiched between the thread anchoring cap 9 and the hub 72, and are retained at the proximal end portion of the pusher tube 7. The assembly of the feeding and deformation means 3 is thus completed.

For the sheath 5, it is possible to use a sheath dwelling after therapy (PCI) or after treatment of a diagnosis (CAG) in which a catheter is used. The distal end portion of the sheath 5 is inserted in a blood vessel.

Then, the feeding and deformation means 3 is inserted into the through-hole 51 of the sheath 5 from the proximal end side of the sheath 5 as shown in FIG. 6, and the hub 62 and the hub 52 are fitted with each other, with the rib 622 of the hub 62 engaging the groove 53 of the hub 52 as shown in FIG. 7. Consequently, the seal portion 41 of the clip 4 projects from the distal end portion of the sheath 5 and is inserted into the blood vessel.

Thereafter, the body element 2 is moved slowly in a direction in which it is pulled out from the wound hole as shown in FIG. 8 until the wound hole and a surrounding portion of the wound hole are covered from the inner side of the blood vessel wall by the seal portion 41 of the clip 4 to position the seal portion 41.

Consequently, the deformation portion 42 and the fastener portion 43 of the deformation portion 42 individually move to the outer side of the blood vessel. Further, the seal portion 41, having been substantially parallel to the fastener portion 43, is guided as it approaches the wound hole by the guide wire 11 so that it is restored towards an orientation in which it is generally perpendicular to the fastener portion 43. Consequently, the wound hole and the surrounding portion of the wound hole are readily and reliably covered.

Figure 9:
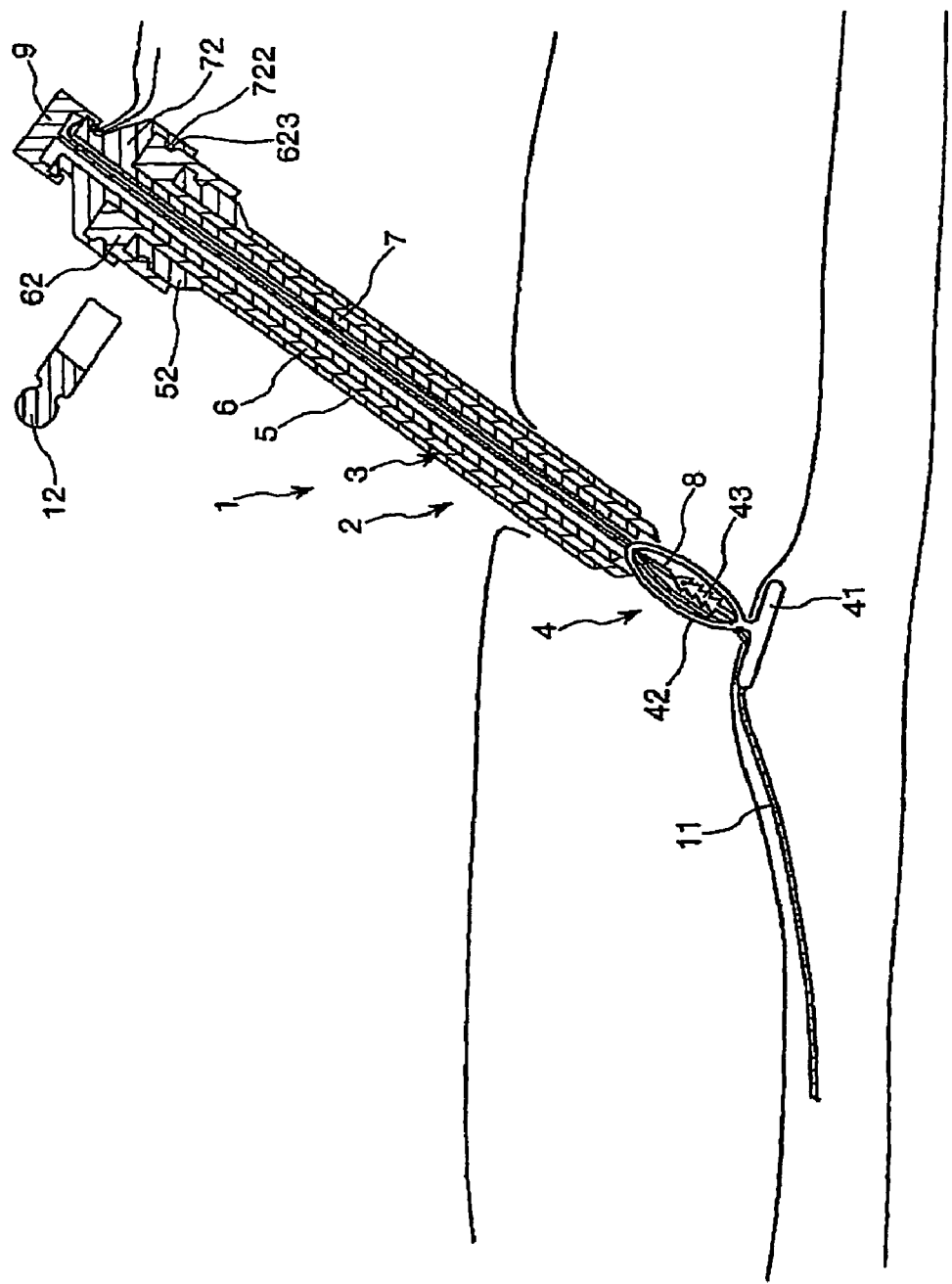
FIG. 9 is a sectional view illustrating a further operational aspect of the tissue closing device shown in FIG. 1.

Then, the stopper 12 positioned between the hub 62 of the covered tube 6 and the hub 72 of the pusher tube 7 is removed, and the covered tube 6 or the sheath is moved in a direction in which it is pulled away from the wound hole until the hub 72 and the hub 62 are fitted with each other, with the rib 722 of the hub 72 engaging the groove 623 of the hub 62 as shown in FIG. 9.

Thereafter, the thread anchoring cap 9 is removed from the hub 72 of the pusher tube 7 so that the guide wire 11 is also pulled off as shown in FIG. 10. Then, while the thread 8 is pulled a little so that tension is applied to the thread 8 (while the fastener portion 43 of the clip 4 is being pulled), the body element 2 is pushed in a direction in which it is inserted into the wound hole to deform the deformation portion 42 of the clip 4 toward the second form (deformed condition). Then, this operation is continued until the staunching operation is completed as shown in FIG. 11.

Consequently, the deformation portion 42 covers the wound hole and the surrounding portion of the wound hole from the outer side of the blood vessel wall while the seal portion 41 covers the wound hole and the surrounding portion of the wound hole from the inner side of the blood vessel wall. Thus, the blood vessel wall is sandwiched between the seal portion 41 and the deformation portion 42 to close the wound hole. Predetermined ones of the pawls 431 of the fastener portion 43 engage the corner portion 421 of the deformation portion 42 to retain the deformation portion 42 in the second form or deformed condition.

Finally, the body element 2 and the thread 8 are pulled off while the clip 4 remains disposed (dwelling) in the living organism. The staunching operation is thus completed.

As described above, according to the living body tissue closing device 1 described above, the safety is relatively high, and the staunching operation can be performed quite readily and with relative certainty for a wound hole formed in a living body tissue membrane such as a blood vessel wall. In other words, the wound hole can be closed (sealed) rather readily and with certainty, and the bleeding can be staunched completely.

A second embodiment of a living body tissue closing device is described below with reference to FIGS. 13-17. It is to be noted that, in FIG. 14, a pusher tube 7 is schematically shown by a broken line.

Further, for the convenience of description, in FIGS. 13, 16 and 17, the left lower side is referred to as the "distal end" and the right upper side is referred to as the "proximal end". Further, in FIGS. 14 and 15, although the upper side of the living body tissue closing device as a whole is the "proximal end" and the lower side is the "distal end", as regards a clip (living body tissue closure) 4, the upper side in the figures is referred to as the "distal end" and the lower side is referred to as the "proximal end".

The following description primarily describes differences between the living body tissue closing device 1 of the second embodiment relative to the first embodiment described above. A detailed description of features common to both embodiments is not repeated.

Figure 14:
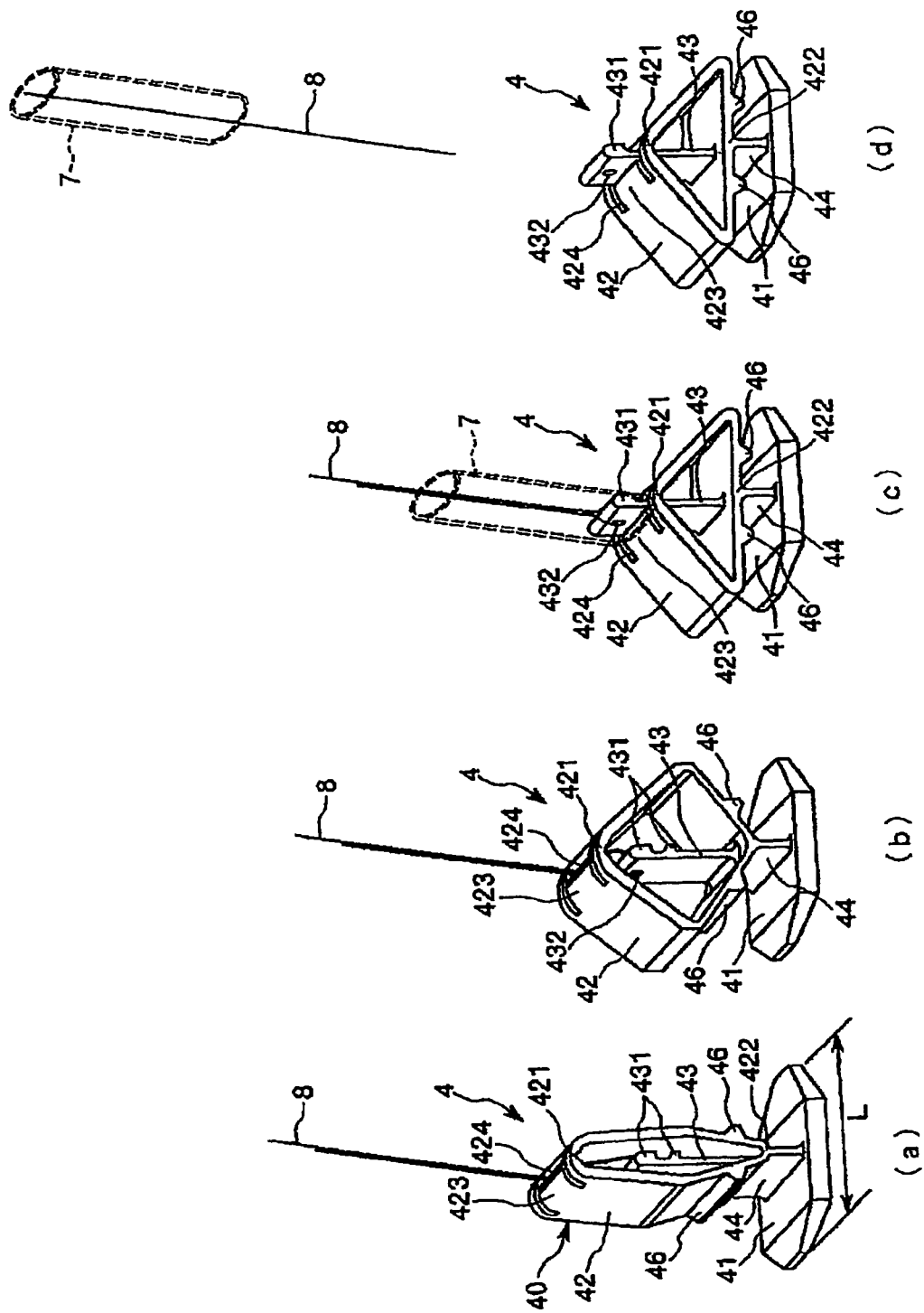

As shown in FIGS. 13 and 14, the living body tissue closing device 1 of the second embodiments does not utilize the guide wire 11.

The clip (living body tissue closure) 4 includes a seal portion 41, a deformable deformation portion 42 adjacent the seal portion 41, a fastener portion 43 for retaining, when the deformation portion 42 enters a state of a predetermined form between a contracted form and an expanded form, the deformation portion 42 in the state of predetermined form, and a connecting portion 44 connecting the seal portion 41 and the deformation portion 42 to each other. The seal portion 41, the deformation portion 42, the fastener portion 43 and the connecting portion 44 are preferably formed integrally in one piece from the same material.

The seal portion 41 is a member having a flat face portion (flat face) for closely contacting a surrounding portion of a wound hole (portion including the wound hole) of a living body tissue membrane from one side (inner surface) of the living body tissue membrane to cover the wound hole and the surrounding portion of the wound hole. In the illustrated embodiment, the seal portion is plate-shaped.

The face (upper side face in FIG. 14) of the seal portion 41 to which the deformation portion 42 is connected is a substantially flat face.

The deformation portion 42 has a shape like a pantograph and is connected (coupled) to a substantially middle portion of the seal portion 41 through the connecting portion 44. In particular, the deformation portion 42 possesses a framework shape and is adapted to be deformed between a contracted form, in which it extends in a direction substantially perpendicular to the seal portion 41 (perpendicular to a reference plane, for example the surface of the seal portion 41 on the deformation portion 42 side) and contracted in a direction substantially parallel to the seal portion 41, and an expanded form in which it extends in a direction substantially perpendicular to the seal portion 41 and is expanded in a direction substantially parallel to the seal portion 41. Accordingly, the deformation portion 42 can be deformed from the basic form (basic shape) shown in FIG. 14(b) to an arbitrary form between the contracted form and the expanded form described above such as a first form shown in FIG. 14(a) wherein it can pass through a wound hole and a second form shown in FIGS. 14(c) and 14(d) wherein the deformation portion 42 cooperates with the seal portion 41 to sandwich the living body tissue membrane therebetween from the other side (outer surface) of the living body tissue membrane. The deformation portion 42 cooperates with the seal portion 41 to sandwich the living body tissue membrane therebetween, with the seal portion positioned on one side of the living body tissue membrane and the deformation portion positioned on the other side of the living body tissue membrane so that the seal portion 41 is held to or retained at the one side of the living body tissue membrane. Accordingly, the deformation portion 42 forms a retainer cooperating with the seal portion 41 to sandwich a living body tissue membrane from the other side of the living body tissue membrane and retain the seal portion 41 to the one side.

Here, in the present embodiment, the deformation portion 42 has a quadrangular annular shape in which a belt-like member includes four bends (a polygonal annular shape). In particular, the deformation portion 42 includes four links formed integrally with each other and arranged in a quadrangular shape (shape of a quadrangular framework) having four corners which can generally bend like a hinge. The deformation portion 42 includes two corner portions 421, 422 positioned at diagonal positions in the upward and downward direction in FIG. 14. The corner portion 422 on the lower side (seal portion 41 side) in FIG. 14 is connected to substantially the middle portion of the seal portion 41 through the connecting portion 44 and thus is a fixed portion which cannot move with respect to the upper side end portion of the connecting portion 44 in FIG. 14 or the fastener portion 43.

The deformation portion 42 is deformed such that the corner portion 421 and the corner portion 422 move toward and away from each other. In particular, the deformation portion 42 can be deformed into expanded and contracted states in two directions perpendicular to each other and can rock (turn around an axis of turning motion) with respect to the seal portion 41. The connecting portion between the seal portion 41 and the corner portion 422 of the deformation portion 42 (the connecting portion 44) possesses flexibility (elasticity), and the seal portion 41 is turned as the connecting portion 44 is bent (resiliently deformed).

The upper face of the corner portion 421 (surface on the opposite side to the seal portion 41) on the upper side (on the opposite side to the seal portion 41) in FIG. 14 is formed as a curved convex face. A substantially H-shaped slit 424 is formed in the corner portion 421 as shown in FIG. 14. The slit 424 forms an opening extending through the deformation portion 42 in the shape of a framework, and at least part of the fastener portion 43 is adapted to be inserted (fitted) into the slit 424. That is, the fastener portion 43 can be accepted in the slit 424.

A pair of projections 46, 46 project from the outer side of the deformation portion 42 on the seal portion 41 side that is in the proximity of the corner portion 422. The projections 46 project toward the seal portion 41 side. Each of the projections 46 extends in a widthwise direction of the deformation portion 42, and a portion of each projection on the seal portion 41 side has a pointed end.

The length of each projection 46 in the widthwise direction of the deformation portion 42 is set substantially equal to the width of the deformation portion 42.

The projections 46 are positioned so that during use of the tissue closure, the projections are located in the proximity of the wound hole closed with the living body tissue closure 4, and the wound hole is tightened strongly by the projections 46. Consequently, the bleeding can be staunched or stopped with a relatively high degree of certainty.

Further, even if a failure occurs in the staunching operation (for example, when the blood vessel wall or the subcutaneous tissue is so hard that the deformation portion 42 cannot be expanded or the like) and manual astriction is required and a force in the direction in which the living body tissue closure 4 is inserted transcutaneously into the blood vessel is applied to the living body tissue closure 4 by the manual astriction, the projections 46 help prevent the living body tissue closure 4 from dropping into the blood vessel. This enhances the safety.

In the illustrated embodiment, the connecting portion 44 is plate-shaped. The connecting portion 44 spaces the seal portion 41 and the corner portion 422 of the deformation portion 42 away from each other by a predetermined distance.

In the illustrated embodiment, the fastener portion 43 is also plate-shaped. The fastener portion 43 is positioned within the framework of the deformation portion 42 and is connected at its proximal end portion (lower side end portion in FIG. 14) to the inner surface of the deformation portion 42. The fastener portion 43 is thus connected to the seal portion 41 through the corner portion 422 and the connecting portion 44. The fastener portion 43 can rock (turn or pivot about a single axis of turning/pivoting motion) together with the deformation portion 42 with respect to the seal portion 41. In other words, the seal portion 41 is able to pivot or turn with respect to the deformation portion 42 and the fastener portion 43 about a single axis (i.e., the relative pivoting/turning movement between the seal portion 41 on the one hand and the deformation portion 42 and fastener portion 43 on the other hand is limited to pivoting/turning movement in a single plane).

The pawls 431 are formed on one side (right side) of the fastener portion 43 in the leftward and rightward direction in FIG. 14. A number (two in the illustrated example) of such pawls 431 are juxtaposed in a spaced relationship by a predetermined distance from each other along the longitudinal direction (upward and downward direction in FIG. 14) of the fastener portion 43.

It is to be noted that the projections 46 of the deformation portion 42 of the clip 4 in terms of, for example, the shape, position and number are not limited to that described above. FIG. 15 illustrates another example in which each of the projections 46 has, as viewed in plan (as viewed from the upper side in FIG. 15), a substantially triangular shape which is pointed toward a central portion of the deformation portion 42 in the widthwise direction.

As shown in FIGS. 14 and 16, the seal portion 41 of the clip 4 is preferably set such that the length L (length in the longitudinal direction) of the longest portion thereof is smaller than the inner diameter (diameter) R of a portion of a living organism lumen (for example, a blood vessel) in which the clip 4 is inserted. More particularly, the length of the longest portion of the seal portion 41 preferably is equal to or less than 6 mm, more preferably equal to or less than 5 mm, and is further preferably approximately 3.5 to 4.5 mm.

Consequently, the seal portion 41 of the clip 4 is permitted to turn (displace) freely with respect to the deformation portion 42 and such advantages are achieved.

As shown in FIG. 16, where a blood vessel is branched intermediately on the distal end side with respect to a wound hole in the blood vessel wall, the seal portion 41 of the clip 4 sometimes interferes with the branched portion of the blood vessel part of the way during the operation in which the body element 2 is moved in a direction in which it is pulled out from the wound hole while the wound hole and a surrounding portion around the wound hole is covered from the inner side of the blood vessel wall with the seal portion 41 of the clip 4 (during positioning of the seal portion 41).

At this time, as shown in FIG. 17, the seal portion 41 can turn with respect to the deformation portion 42 and be brought away from interfering with the branched portion of the blood vessel. Consequently, the seal portion 41 can be prevented from being caught or being stuck by the branched portion of the blood vessel.

Further, since the seal portion 41 can turn around only one axis of pivoting motion (i.e., is limited to pivoting movement in a single plane) with respect to the deformation portion 42 (being bent in only one fixed direction), the seal portion 41 can be moved readily and stably along the route of the blood vessel. Finally, the seal portion 41 can be positioned at an optimum position with respect to the wound hole of the blood vessel wall, for example can be positioned such that the longitudinal direction of the seal portion is in substantially parallel relation to the route of the blood vessel. Consequently, the bleeding can be staunched with a relatively high degree of certainty.

Further, since positioning of the seal portion 41 can be performed only by inserting the living body tissue closure 4 once into the deepest portion of the blood vessel on the central side and then moving the body element 2 in a direction in which it is pulled off from the wound hole, the staunching operation can be performed very readily and with certainty.

With the living body tissue closing device 1, similar effects to those of the living body tissue closing device 1 of the first embodiment described hereinabove can be achieved.

Figure 19:
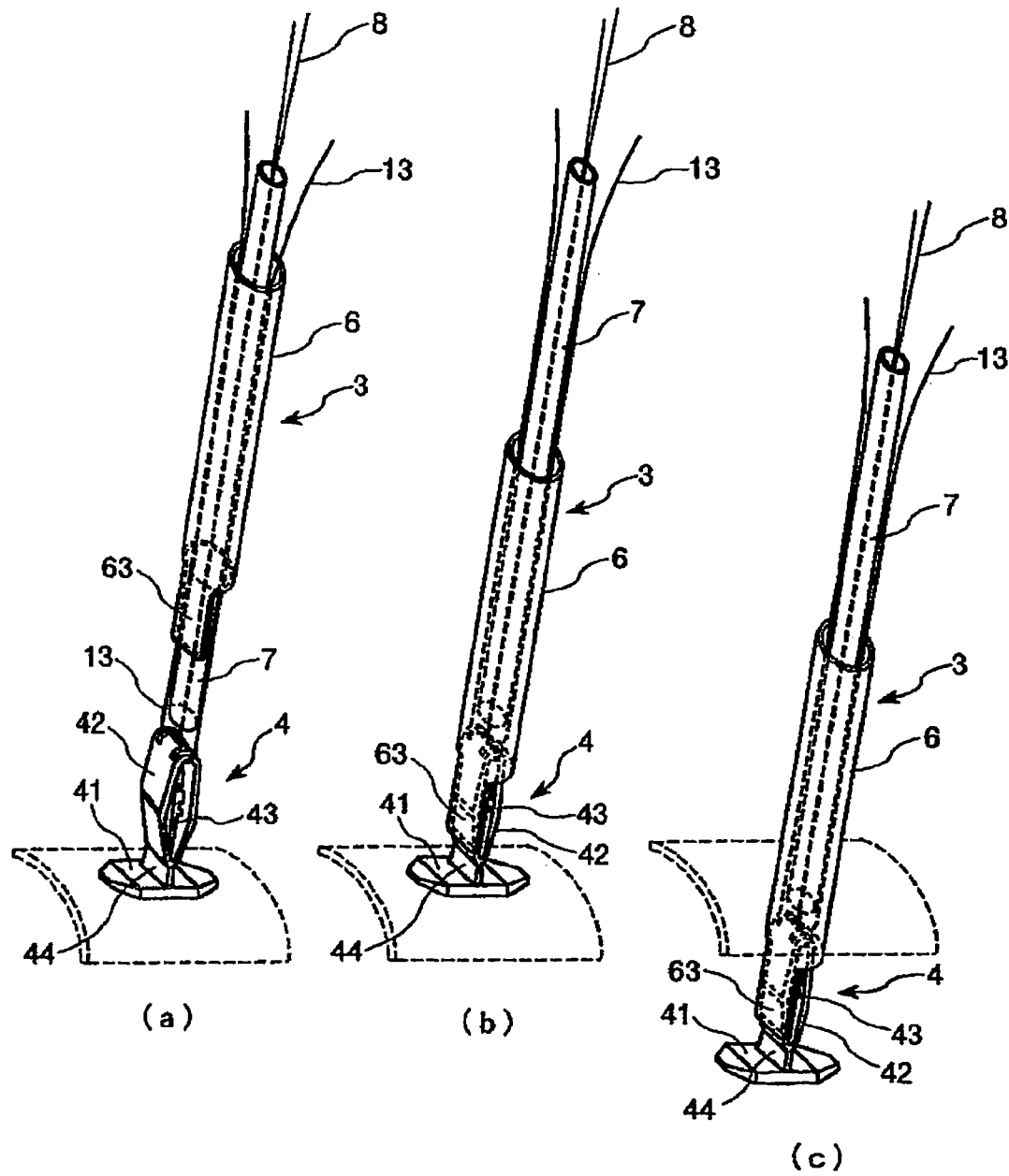
Figure 20:
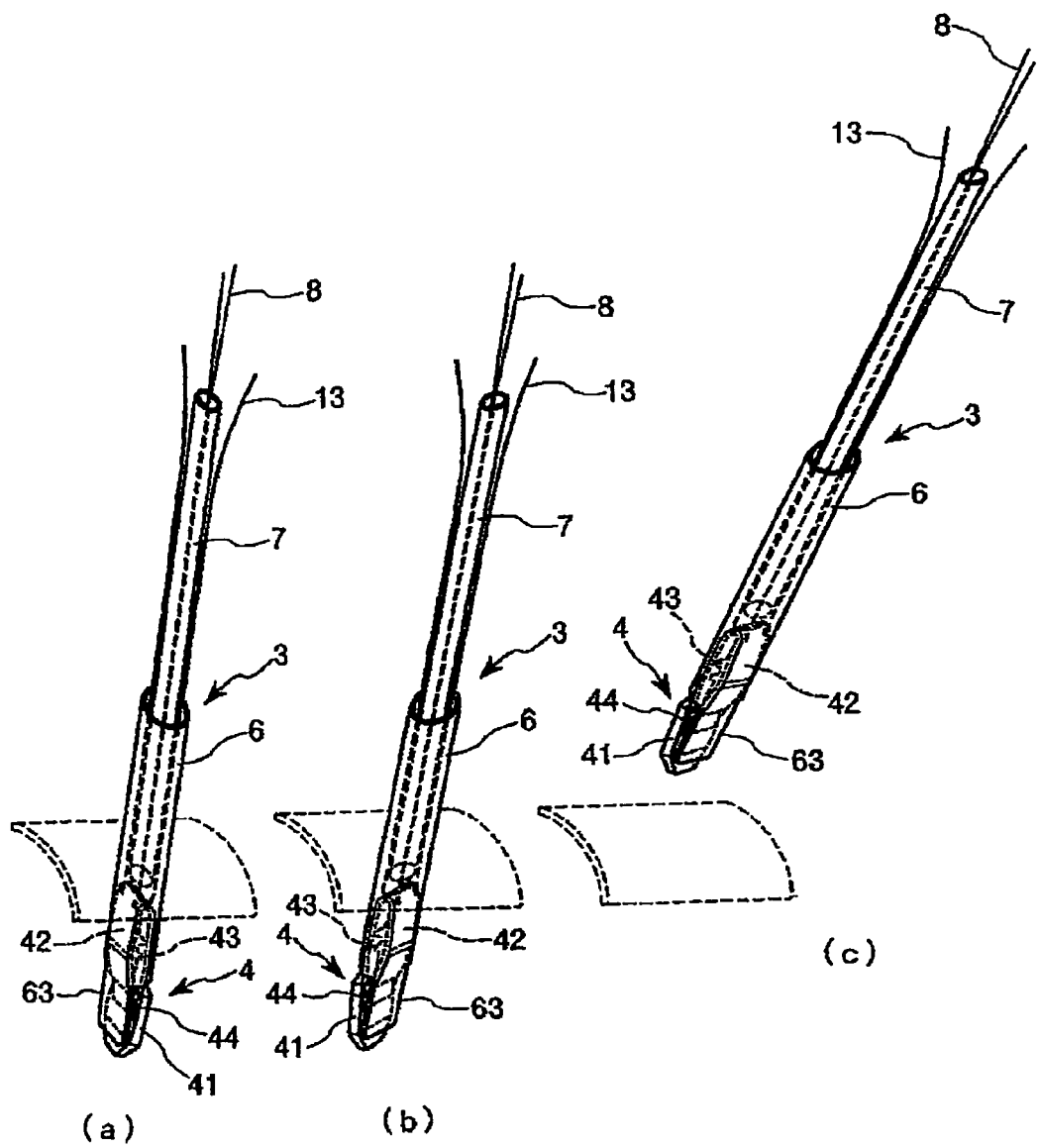

A third embodiment of a living body tissue closing device will now be described with reference to FIGS. 18-20. In FIGS. 18-20, the proximal end side of each of the covered tube 6 and the pusher tube 7 is not shown.

For the convenience of description, in FIGS. 18-20, the left lower side is referred to as the "distal end" and the right upper side is referred to as the "proximal end". Regarding the clip (living body tissue closure) 4, the upper side in the figures is referred to as the "distal end" and the lower side is referred to as the "proximal end".

The following description primarily describes differences between the living body tissue closing device 1 of the third embodiment relative to the second embodiment described above. A detailed description of features common to both embodiments is not repeated.

As shown in FIG. 18, the living body tissue closing device 1 includes a thread (string member) 13 serving as deformation portion pulling means for pulling the deformation portion 42 of the clip 4 to the proximal end side of the feeding and deformation means (arrangement device) 3.

In a state in which the thread 13 is threaded through the deformation portion 42 and suspended on the corner portion 421, the opposite end portions thereof are drawn out from the proximal end side of the covered tube 6 and the pusher tube 7 to the outside. The thread 13 forms a retainer for retaining (accommodating) the deformation portion 42 of the clip 4 at the distal end portion of the covered tube 6 (on the distal end side of the feeding and deformation means 3).

The covered tube 6 has a contacting portion 63 provided at the distal end portion of the tube body 61. The contacting portion 63 is plate-shaped and projects in the direction of the distal end from the distal end of the tube body 61. That is, in the illustrated embodiment, the contacting portion 63 is formed by a distally extending extension of a part of the wall portion forming the tube body 61.

In the disclosed and illustrated example, the contacting portion 63 is preferably formed such that it satisfies the relationship a>L, where a is the length of the contacting portion 63 in the longitudinal direction and L is the length in the longitudinal direction of the longest portion of the deformation portion 42.

The contacting portion 63 forms a displacement means for displacing the seal portion 41 of the clip 4 so that it extends substantially parallel to the longitudinal direction (axial direction) of the feeding and deformation means (arrangement device) 3.

With this embodiment of the living body tissue closing device 1, the clip 4 inserted in a blood vessel (living organism lumen) can be recovered from within the blood vessel part of the way through the staunching operation.

The following is a description of the operation of the living body tissue closing device 1 is a situation when the clip 4 is positioned such that the seal portion 41 of the clip 4 is positioned within a blood vessel while the deformation portion 42 and the fastener portion 43 are positioned outside the blood vessel as shown in FIG. 18.

First, the thread 13 is pulled to the proximal end side of the feeding and deformation means 3 to pull the deformation portion 42 of the clip 4 to the proximal end side and deform the deformation portion 42 so that the deformation portion 42 is expanded in a direction substantially perpendicular to the seal portion 41 and is contracted in a direction substantially parallel to the seal portion 41 (so as to be closed) as shown in FIG. 19(a).

Then, while the thread 13 is pulled to the proximal end side of the feeding and deformation means 3 to pull the deformation portion 42 of the clip 4 to the proximal end side, the covered tube 6 is pushed out or advanced in the distal direction until the deformation portion 42 is retained (accommodated) in the proximal end portion of the covered tube 6 as shown in FIG. 19(b).

The feeding and deformation means 3 is then moved in the distal direction so that the proximal end portion of the covered tube 6 enters into the blood vessel until the seal portion 41 is positioned at a position at which the seal portion 41 of the clip 4 can turn as shown in FIG. 19(c). That is, the seal portion 41 is moved away from the inner surface of the blood vessel wall in which the wound hole is formed as shown in FIG. 19(c).

Thereafter, while the thread 13 is being pulled to the proximal end side of the feeding and deformation means 3 (while the deformation portion 42 of the clip 4 is being pulled to the proximal end side), the covered tube 6 is pushed out (propelled) in the distal direction as shown in FIG. 20(a). Consequently, the face of the seal portion 41 on the deformation portion side contacts the contacting portion 63. The seal portion 41 thus turns (is displaced) with respect to the deformation portion 42 until it comes to a position in which it extends substantially parallel to the longitudinal direction (axial direction) of the covered tube 6 (feeding and deformation means 3).

Then, the covered tube 6 is turned by approximately 180° so that the upper side end portion of the seal portion 41 in FIG. 20(b) can be readily pulled out from the wound hole or the wound of the blood vessel.

Finally, the feeding and deformation means 3 and the clip 4 are pulled out from the wound hole or wound of the blood vessel as shown in FIG. 20(c). By the procedure described above, the clip 4 is recovered from within the blood vessel. Thereafter, predetermined treatment such as manual astriction can be performed.

With the living body tissue closing device 1 of the third embodiment, similar effects to those of the living body tissue closing device 1 of the second embodiment described hereinabove are achieved.

Further, even if the deformation portion 42 of the clip 4 does not open (for example, when the blood vessel is hard due to calcification, when the subcutaneous tissue has a hard trace by re-punctures or the like) and failure in staunching the bleeding occurs, the clip 4 inserted in the blood vessel can be readily recovered and with certainty from within the blood vessel. Thereafter, ordinary manual astriction, for example, can be preformed. Consequently, the safety is enhanced significantly.

The living body tissue closing device disclosed herein by way of several embodiments makes it possible to readily perform a staunching operation for a wound hole formed in a living body tissue membrane such as a blood vessel wall with a relatively high degree of certainty and safety. The wound hole can be closed rather readily and with relative certainty, with the bleeding staunched or stopped completely.

As described above, the clip 4 preferably possesses certain characteristics which are useful in the context of the disclosed usage. For example, it has been mentioned that the clip preferably possesses good hinge characteristics. The material from which the clip 4 is made is also a consideration. Collagen has been used for years for surgical operations and the like as a haemostatic material. Collagen is generally known to promote blood coagulation by activating the blood platelet to stop bleeding from the blood vessel. While collagen is well suited to stopping bleeding, it has been found that a thrombus can be formed by contact of collagen and blood inside the blood vessel, thus causing a vascular obstruction when collagen is inserted in the blood vessel. Thus concerns might arise using a collagen clip in the tissue closing device.

An experiment was conducted using a clip made of polydioxanone (PDO). The experiment was conducted on a pig weighing approximately 50 kg. The femoral artery of the pig was exposed by an incision made around the thigh of the pig while the pig was under continuous inhalation anesthesia. A sheath was placed in the exposed femoral artery. Two hundred units/kg of heparin was administered as an anti-coagulation agent. A clip made of PDO was introduced through the sheath and placed in the artery. The bleeding from the puncture hole made by the sheath was stopped, and after confirming that the bleeding had stopped, the incision in the thigh was sutured. Following completion of suturing, the pig was released from the inhalation anesthesia.

Twelve days after placement of the clip, the pig was sacrificed by blood letting under continuous inhalation anesthesia. The femoral artery in which the clip had been placed was removed and was subject to formalin fixation, and the formalin-fixed femoral artery was pathologically observed. The results of the observation showed no thrombosis formation.

It has thus been found that PDO, which has been previously used for suturing general soft tissues including infant cardiovascular tissues, is a particularly preferred material for the clip 4 used in the tissue closing device in that such material reduces the possibility of the formation of a thrombosis at the site where the clip contacts the blood, thus reducing the likelihood of a vascular obstruction. The clip made of this material can thus be inserted in the blood vessel through a procedure sheath that is kept in place in the blood vessel after being previously used for catheter surgery.

An experiment was conducted to compare characteristics of a clip having a seal portion made of PDO and a commercially available vascular closure device that includes a seal portion made of a copolymer of polyglycolic acid and polylactic acid and a collagen plug that is attached to the seal portion with thread. The seal portion of the commercially available product was kept in about 50 ml of a phosphate buffer solution (pH 7.41) in a screw cap test tube. After a cap of the screw cap test tube was closed, the tube was placed in an oven at 37° C. On days 7 and 14, and external observation and a strength measurement were performed. A seal portion 41 made of PDO was similarly tested. The strength measurement in this example measured the destruction strength by pulling the upper top portion of the deformation portion while the seal portion was fixed. The results of this experiment are shown in the table below.

| Samples | Day 7 | | Day 14 | |
| --- | --- | --- | --- | --- |
| | External Observation | Strength | External Observation | Strength |
| Commercially available product | Swollen and softened | Not Measured | Deformed | Not Measured |
| Clip having Seal Portion made of PDO | No Change | 3.5 kgf | No Change | 3.2 kgf |

The seal portion of the commercially available product kept dipped in a phosphate buffer solution (pH 7.4) at 37° C. caused the seal portion to swell and deform on day 7 and lose its strength significantly. On the other hand, the seal portion made of PDO, and smaller in size than that of the commercially available product, did not swell while kept dipped in a phosphate buffer solution (pH 7.4) at 37° C., and maintained its strength. It has been demonstrated that the seal portion made of PDO maintains relatively secure hemostatic capability more safely during the time period that the seal portion placed in the blood vessel is encapsulated to be stable (approximately 1 week).

Another aspect of the tissue closure which has been studied is the size of the seal portion 41 of the clip 4. Since the seal portion is introduced through a sheath, the width of the seal portion should preferably be one that allows the clip to be moved or transited inside the sheath. The width of the seal portion 41 refers to the dimension of the seal portion perpendicular to the length L of the seal portion shown in FIG. 18. It has been found that the width of the seal portion 41 should preferably be one-half or less of the length of the inner circumference of the sheath. For example, when the sheath possesses a size used for a 6 French (Fr) catheter (i.e., the size of the sheath is greater than the size of the catheter inserted in the sheath), the width of the seal portion should preferably be 3.5 mm or less. When the sheath possesses a size used for a 7 Fr catheter, the width should preferably be 4.0 mm or less. When the sheath possesses a size used for a 8 Fr catheter, the width should preferably be 4.5 mm long or less. Note that 1 French (Fr) is equal to 0.33 mm (0.013 inches) for the outer diameter of a tube. By way of example, the inner diameter of the sheath used for a 6 Fr catheter is 2.22 mm.

Alternatively, the sheath into which the seal portion 41 is introduced may be fixed to its sheath hub by a hollow pin that is axially inserted or embedded in the hub for the sheath (i.e., the proximal end of the sheath and the distal end of the hub are fitted to one another, and a pin with an increasing outer size is fitted into the distal end of the hub and the proximal end of the sheath to fix the sheath and hub relative to one another). In such a situation, the width of the seal portion should preferably be equal to or less than the inner diameter of the pin. For example, when the sheath possesses a size used for a 6 Fr catheter, the width of the seal portion should preferably be 2.8 mm or less. When the sheath possesses a size used for a 7 Fr catheter, the width should preferably be 3.2 mm long or less. When the sheath possesses a size used for a 8 Fr catheter, the width should preferably be 3.7 mm long or less.

The length of the seal portion of the clip is another consideration. The length of the seal portion refers to the dimension identified as L in FIG. 18. The length of the seal portion should be smaller than the inner diameter of the blood vessel where the blood staunching operation is performed so that the seal portion does not damage the blood vessel wall and so that the seal portion does not become stuck at a vascular bifurcation when the seal portion moves inside the blood vessel.

The length of the seal portion should also be larger than the outer diameter of the sheath so that the seal portion is able to block or cover the puncture hole made by the sheath that is inserted in the blood vessel. In addition, the seal portion should be dimensioned so that it is not pulled out from the blood vessel by the force of the operator (approximately 400 gf) that is applied by the operator to determine that the seal portion is positioned around the puncture hole of the blood vessel.

The length of the seal portion should thus preferably be equal to or greater than the outer diameter of the sheath, and equal to or less than the inner diameter of the blood vessel. For example, when the sheath possesses a size used for a 6 Fr catheter, the length of the seal portion should preferably be equal to or greater than 2.5 mm, and equal to or less than 8.0 mm. When the sheath possesses a size used for a 7 Fr catheter, the length of the seal portion should preferably be equal to or greater than 2.9 mm, and equal to or less than 8.0 mm. When the sheath possesses a size used for a 8 Fr catheter, the length of the seal portion should preferably be equal to or greater than 3.2 mm, and equal to or less than 8.0 mm long or less.

An experiment was performed on clips with sealing portions of different dimensions. A sheath was placed in the femoral artery of a cadaver and the clips were introduced through the sheath into the blood vessel. For each clip, the clip was pulled until a predetermined resistance was felt. Then, it was confirmed whether the seal portion of the clip was contacting the blood vessel at the puncture hole made by the sheath or whether instead the seal portion of the clip was stuck inside the blood vessel.

After the positioning was completed, the portion of the clip outside the blood vessel was attached to a spring gage and a pulling force of 400 gf was applied to the clip. It was then determined whether the clip was pulled out of the blood vessel upon applying this pulling force. The results of the experiment for clips with sealing portions of different dimensions are set forth in the table below.

| Sheath for Receiving a Catheter of Noted Size | Width of the Seal Portion | Length of the Seal Portion | Whether or not the clip was stuck inside the blood vessel | Whether or not the seal portion was pulled out upon pulling with a force of 400 gf |
|---|---|---|---|---|
| 6Fr | 2.7 mm | 10 mm | Yes | Not observed (Determined to be unnecessary to observe) |
| 6Fr | 3.0 mm | 6 mm | No | Not observed (Determined to be unnecessary to observe) |
| 6Fr | 2.8 mm | 5 mm | No | Not pulled out |
| 6Fr | 2.8 mm | 4 mm | No | Not pulled out |

Since the outer diameter of the sheath used for a 6 Fr catheter is 2.6 mm, a seal portion with a length of 3 mm long was determined to be obviously pulled out and was thus not observed. That is, because the differential between the outer diameter of the sheath (i.e., the size of the wound hole) and the 3 mm length of the seal portion is quite small, it was determined that the seal portion would obviously be pulled out. Also, as it was observed that the seal portion with a length of 5 mm was not pulled out, it was determined that seal portions with a length of 6 mm and a length of 10 mm would also not be pulled out and so were not observed.

As a result of the experiment, it has been found that when the seal portion is introduced through a sheath having a size for 6 Fr-8 Fr catheters, and is intended to be positioned inside the femoral artery, the length of the seal portion should preferably be equal to or greater than 4.0 mm, and equal to or less than 6.0 mm.

Another consideration involving the sealing portion is determining a size of the sealing portion that will prevent the clip from becoming caught in and hurting the intima of the blood vessel. When the seal portion of the clip is moved inside the blood vessel, it is desirable that the seal portion not get stuck in the blood vessel, while still being able to be positioned around the puncture hole such that when the seal portion is pulled with a predetermined force, the seal portion is not pulled out of the puncture hole.

The seal portion of the clip includes a front end portion (the end nearer to the heart or on the upstream side of blood flow) and a rear end portion. The front end portion of the seal portion refers to the end portion that is nearer to the heart and on the upstream side of blood flow. The rear end portion refers to the end portion that is nearer to the peripheral (i.e., the end portion farther away from the heart) and on the downstream side of blood flow. It has been found that if both end portions of the seal portion are of the same length, the front end portion of the seal portion can become caught and hurt the intima of the blood vessel, thus causing trauma, damage and/or bleeding in the blood vessel. It has been discovered that this may be addressed by elongating or increasing the length of the front end portion of the seal portion more than the rear end portion of the seal portion. The reasons are thought to be as follows. The distal end of the sheath used in the heart-catheterization surgery is placed in the blood vessel facing the heart, and the puncture cavity of the subcutaneous tissue slopes along the vessel as shown schematically in FIG. 21. When the seal portion is pulled together with the sheath to position the seal portion to the blood vessel, the connecting portion 44 of the seal portion pushes and opens the puncture hole of the blood vessel toward the end nearer to the peripheral. Then, since a torque which rotates the seal portion occurs, the front end portion moves up and the rear end portion moves down. Accordingly, there is a likelihood that the front end portion of the seal portion will be caught in and hurt the blood vessel wall.

It is thought that making the length of the front end portion of the seal portion longer than the rear end portion, making the front end portion of the seal portion a certain length (minimum length) and enlarging the contact area of the front end portion to the vessel wall could help avoid damage to the blood vessel surface.

An experiment was performed in which a sheath was placed in the femoral artery of a cadaver. A clip was introduced through the sheath into the blood vessel. The clip was clipped to the puncture hole made by the sheath (i.e., the clip was operated to sandwich the blood vessel wall between the seal portion and the deformation portion) using the procedures discussed above in connection with the several disclosed embodiments. After removing the blood vessel to which the clip was applied, the status of the inner surface of the blood vessel in the area of the seal portion was observed. This experiment was conducted with two clips, one having a seal portion length of 4 mm with the front and rear end portions each being 2 mm in length, and another having a seal portion length of 5 mm with the front end portion having a length of 3 mm and the rear end portion having a length of 2 mm. The results are set forth in the table below.

| Length of the Seal Portion | Length of the Front/Rear End Portion | Whether or not the front end portion of the seal portion gave trauma to the surface of the blood vessel |
|---|---|---|
| 4 mm | 2 mm/2 mm | Yes |
| 5 mm | 3 mm/2 mm | No |

The results of the experiment confirmed that damage to the blood vessel surface could be lessened or avoided by making the length of the front end portion of the seal portion longer than the rear end portion, making the front end portion of the seal portion a certain length (minimum length) and enlarging the contact area of the front end portion to the vessel wall. It was found that the length of the front end portion of the seal portion is preferably equal to or greater than 3 mm.

Another aspect of the clip to be considered involves the length of the outside portion of the clip from the blood vessel. The length of the outside portion of the clip from the blood vessel (the length of the deformation portion) should preferably be shorter than that of the puncture cavity from the skin to the blood vessel in order to avoid infection or breakdown of the clip, since the outside portion is exposed to the outside environment of the body. The length of the outside portion of the clip from the blood vessel is preferably equal to or less than 20 mm, more preferably equal to or less than 10 mm, to shorten the distance for the blood vessel to travel by pulling the clip (i.e., the moving distance of the deformation portion for deformation) upon carrying out the clipping operation described above in connection with the several disclosed embodiments. The moving distance of the deformation portion refers to the distance between the position of the seal portion shown in FIG. 9 and the position of the seal portion shown in FIG. 11, because as the deformation portion is deformed during the clipping operation shown in FIGS. 9-11, the movement of the seal portion 41 causes the blood vessel to be pulled up.

A further consideration that arises when positioning the clip in the blood vessel during the clipping operation is the retaining force that the covered tube applies to retain the deformation portion. If this retaining force, involving the frictional force between the deformation portion 42 and the covered tube 6, is excessively small, the deformation portion 42 can draw out easily from the covered tube. On the other hand, if the retaining force is excessively large, it will be difficult to draw the deformation portion 42 out of the covered tube 6.

An experiment was conducted to determine the force required to pull the seal portion out of the blood vessel. In this experiment, a sheath was placed in the femoral artery of a cadaver and a clip was introduced through the sheath into the blood vessel. The clip was positioned at the puncture hole made by the sheath by the procedures described above. After positioning the clip, the portion of the clip outside the blood vessel was attached to a spring gage. The spring gage was then pulled and the force was measured when the seal portion of the clip was pulled out of the blood vessel. The results are shown in the table below.

| Sheath Placement | Length of the Seal Portion | Length of the Front/Rear End Portion | Force for pulling the seal portion out of the blood vessel |
|---|---|---|---|
| Exposed blood vessel | 5 mm | 3 mm/2 mm | 1.2 kgf |
| Subcutaneous blood vessel | 5 mm | 3 mm/2 mm | 2.2 kgf |

It was demonstrated that the seal portion was pulled out of the blood vessel when the seal portion was pulled away from the blood vessel with a force of 2.2 kgf or more after positioning of the seal portion. Therefore, the retaining force that the covered tube 6 applies to retain the deformation portion (i.e., the force by which the deformation portion is pulled out from the covered tube 6) should preferably be less than 2.2 kgf, more preferably less than 1.2 kgf, to reduce damage to the blood vessel with the seal portion and to expand the range of application.

Other properties of the clip that have been found to be of significance include the breaking force of the connecting portion between the seal portion and the deformation portion. Here, the breaking force of the connecting portion should preferably be 2.0-5.0 kgf/mm$^2$. In addition, the force required to deform the deformation portion should preferably be 0.3-1.0 kgf (0.2-0.3 mm thickness of the hinges forming the deformation portion)

It is to be understood that the each of the embodiments described above can be configured to include features from the other embodiments.

Also, the fastener portion 43 may be a filament that passes through from the inner side of the deformation portion 42 to the corner portion 421. The filament may fix the deformation portion 42 by a knot on the upper side of the corner portion 421. Also, the seal portion 41 may have such a structure (configuration) as that of the deformation portion 42 described hereinabove.

The description above describes principles and preferred embodiment of the disclosed living body tissue closing device. However, the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A tissue closure for closing an opening penetrating a tissue membrane comprising:
    a seal portion configured to cover the opening penetrating a tissue membrane and a surrounding portion of the opening from one side of the tissue membrane;
    a framework body portion deformable between a contracted form in which the framework body portion is extended in a direction substantially perpendicular to a reference plane and is contracted in a direction substantially parallel to the reference plane and an expanded form in which the framework body portion is contracted in the direction substantially perpendicular to the reference plane and is expanded in the direction substantially parallel to the reference plane, the seal portion and the framework body portion being integrally molded in one piece from a bioabsorbable material; and
    a connecting portion connecting the seal portion and the framework body portion, the connecting portion consisting of a single bendable plate so that the connecting portion permits pivoting motion of the seal portion in only a single plane.

2. The tissue closure according to claim 1, further comprising a fastener portion configured to retain the framework body portion when the framework body portion is in a predetermined form between the contracted form and the expanded form.

3. The tissue closure according to claim 1, wherein the framework body portion possesses a height when the framework body portion is contracted form, the height of the framework body portion is equal to or less than 10 mm.

4. A tissue closing device for closing an opening which penetrates a tissue membrane, comprising:
    an elongated body element having a distal end portion configured to pass though the opening;
    a tissue closure removably mounted at a distal end portion of the body element and configured to pass through the opening together with the distal end portion of the body element to close the opening; and
    deformation means for deforming a portion of the tissue closure;
    the tissue closure comprising:
        a seal portion for covering the opening and a surrounding portion of the opening from one side of the tissue membrane;
        a deformation portion deformable to a first form in which the deformation portion is configured to pass through the opening and deformable by the deformation means to a second form in which the deformation portion is positioned on a side of the tissue membrane opposite the one side and cooperates with the seal portion to sandwich the tissue membrane between the seal portion and the deformable portion;

a fastener portion for retaining the deformation portion in the second form;

the deformation portion is connected to the seal portion by a connecting portion which is configured to be positioned in the opening penetrating the tissue membrane when the tissue membrane is sandwiched between the seal portion and the deformation portion, the connecting portion consisting of a single bendable plate so that the connecting portion permits pivoting motion of the seal portion in only a single plane; and the seal portion and the deformation portion being integrally molded in one piece from a bioabsorbable material.

5. The tissue closing device according to claim 4, wherein the deformation portion possesses a framework shape.

6. The tissue closing device according to claim 5, wherein the deformation portion has an opening portion configured to receive at least a part of the fastener portion as the deformation portion is deformed to the second form.

7. The tissue closing device according to claim 6, wherein the fastener portion comprises at least one pawl insertable into the opening portion and engageable with the deformation portion.

8. The tissue closing device according to claim 4, wherein the deformation portion possesses a quadrangular shape formed integrally from four links and is deformable such that two corner portions at diagonally opposite positions of the quadrangular shape move toward and away from each other.

9. The tissue closing device according to claim 8, wherein the fastener portion is configured to control a distance between the two corner portions.

10. The tissue closing device according to claim 8, wherein the fastener portion is constructed to control a distance between the two corner portions to any one of a plurality of different distances.

11. The closing device according to claim 4, wherein the fastener portion is constructed to control a degree of deformation of the deformation portion to one of a plurality of deformed states.

12. The tissue closing device according to 4, wherein the fastener portion is constructed to allow deformation of the deformation portion in a direction in which a degree of deformation of the deformation portion increases while also preventing deformation of the deformation portion in another direction in which the degree of deformation of the deformation portion decreases.

13. The tissue closing device according to claim 4, wherein the seal portion is plate shaped.

14. The tissue closing device according to claim 4, wherein the fastener portion, the seal portion and the deformation portion are integrally molded in one piece from the same material.

15. The tissue closing device according to claim 4, wherein the fastener portion and the deformation portion are individually inclined with respect to the seal portion.

16. The tissue closing device according to claim 4, wherein the tissue closure is provided with a hole through which a guide wire is to pass.

17. The tissue closing device according to claim 4, further comprising pulling means for pulling the tissue closure, the deformation portion being deformed by the deformation means while the tissue closure is being pulled by the pulling means.

18. The tissue closing device according to claim 17, wherein the pulling means is a string.

19. The tissue closing device according to claim 18, wherein the fastener portion has a hole through which the string is to be threaded.

20. The tissue closing device according to claim 4, wherein the deformation means presses the deformation portion to deform the deformation portion into the second form.

21. The tissue closing device according to claim 4, wherein at least a portion of the deformation means is a tubular member provided on the body element.

22. The tissue closing device according to claim 4, wherein the tissue membrane is a blood vessel wall, and the one side is an inner surface of the blood vessel wall while the side opposite the one side is an outer surface of the blood vessel wall.

* * * * *